US012630876B2

(12) United States Patent
Ye et al.

(10) Patent No.: US 12,630,876 B2
(45) Date of Patent: May 19, 2026

(54) KIT FOR GENOTYPING OF PLATELET AND NEUTROPHIL ANTIGENS AND GLYCOPROTEINS

(71) Applicant: Shanghai Blood Center, Shanghai (CN)

(72) Inventors: Luyi Ye, Shanghai (CN); Huijun Zhu, Shanghai (CN); Ruishu Li, Shanghai (CN); Min Fu, Shanghai (CN); Ping Lu, Shanghai (CN); Ziyan Zhu, Shanghai (CN)

(73) Assignee: SHANGHAI BLOOD CENTER, Shanghai (CN)

( * ) Notice: Subject to any disclaimer, the term of this patent is extended or adjusted under 35 U.S.C. 154(b) by 609 days.

(21) Appl. No.: 18/156,739

(22) Filed: Jan. 19, 2023

(65) Prior Publication Data

US 2023/0235390 A1     Jul. 27, 2023

(30) Foreign Application Priority Data

Jan. 26, 2022    (CN) .......................... 202210098023.5

(51) Int. Cl.
| | |
|---|---|
| *C12P 19/34* | (2006.01) |
| *C12Q 1/6806* | (2018.01) |
| *C12Q 1/6853* | (2018.01) |
| *C12Q 1/6872* | (2018.01) |

(52) U.S. Cl.
CPC ......... *C12Q 1/6872* (2013.01); *C12Q 1/6806* (2013.01); *C12Q 1/6853* (2013.01); *C12Q 2600/156* (2013.01); *C12Q 2600/16* (2013.01)

(58) Field of Classification Search
CPC .................................................. C12Q 1/6881
See application file for complete search history.

(56) References Cited

U.S. PATENT DOCUMENTS

2008/0261205 A1* 10/2008 Denomme ............. C07H 21/04
                                              435/6.16
2010/0055706 A1*  3/2010 Greinacher ........ G01N 33/6854
                                              435/5

FOREIGN PATENT DOCUMENTS

| CN | 110172502 A | 8/2019 | |
|---|---|---|---|
| CN | 111455027 A | 7/2020 | |
| WO | WO-0136675 A2 * | 5/2001 | ........... C12Q 1/6883 |
| WO | WO-2012083481 A1 * | 6/2012 | ........... C12Q 1/6883 |

* cited by examiner

*Primary Examiner* — Kenneth R Horlick
(74) *Attorney, Agent, or Firm* — MUNCY, GEISSLER, OLDS & LOWE, P.C.

(57) ABSTRACT

The present invention provides a mass spectrometry-based method and a kit for genotyping of platelet and neutrophil antigens and glycoproteins, which are used for genotyping of platelet-specific antigens, platelet CD36 glycoproteins and neutrophil antigens; by designing an optimal primer combination, problems such as homologous sequences and rich GC are overcome, moreover, by improving amplification reaction conditions and using nucleic acid mass spectrometry as a platform, 35 platelet-specific antigen polymorphic sites, 10 CD36 polymorphic sites and 8 neutrophil antigen polymorphic sites can be simultaneously detected in 2 reactions. The present invention has the characteristics of high specificity and sensitivity, and fast and high throughput, and can be used in clinic, scientific research, platelet donor routine screening, etc.

7 Claims, 12 Drawing Sheets
Specification includes a Sequence Listing.

SEQUENCE LISTING

```
Sequence total quantity: 181
SEQ ID NO: 1            moltype = DNA   length = 35
FEATURE                 Location/Qualifiers
source                  1..35
                        mol_type = other DNA
                        organism = synthetic construct
SEQUENCE: 1
acgttggatg ggaacaaaat caaattagca acagc                               35

SEQ ID NO: 2            moltype = DNA   length = 33
FEATURE                 Location/Qualifiers
source                  1..33
                        mol_type = other DNA
                        organism = synthetic construct
SEQUENCE: 2
acgttggatg ttttaatgac taacagctgc aaa                                 33

SEQ ID NO: 3            moltype = DNA   length = 23
FEATURE                 Location/Qualifiers
source                  1..23
                        mol_type = other DNA
                        organism = synthetic construct
SEQUENCE: 3
cttcagattc tttaatactc tgt                                            23

SEQ ID NO: 4            moltype = DNA   length = 30
FEATURE                 Location/Qualifiers
source                  1..30
                        mol_type = other DNA
                        organism = synthetic construct
SEQUENCE: 4
acgttggatg aggcacagaa gtttacagac                                     30

SEQ ID NO: 5            moltype = DNA   length = 29
FEATURE                 Location/Qualifiers
source                  1..29
                        mol_type = other DNA
                        organism = synthetic construct
SEQUENCE: 5
acgttggatg ggactcactc acctgtacg                                      29

SEQ ID NO: 6            moltype = DNA   length = 21
FEATURE                 Location/Qualifiers
source                  1..21
                        mol_type = other DNA
                        organism = synthetic construct
SEQUENCE: 6
attcaagtta agcaaagagg t                                              21

SEQ ID NO: 7            moltype = DNA   length = 30
FEATURE                 Location/Qualifiers
source                  1..30
                        mol_type = other DNA
                        organism = synthetic construct
SEQUENCE: 7
acgttggatg gaaaatgtaa cccaggacgc                                     30

SEQ ID NO: 8            moltype = DNA   length = 30
FEATURE                 Location/Qualifiers
source                  1..30
                        mol_type = other DNA
                        organism = synthetic construct
SEQUENCE: 8
acgttggatg actgtgaagt tgtcagcctc                                     30

SEQ ID NO: 9            moltype = DNA   length = 18
FEATURE                 Location/Qualifiers
source                  1..18
                        mol_type = other DNA
                        organism = synthetic construct
SEQUENCE: 9
aggacgctga ggacaaca                                                  18

SEQ ID NO: 10           moltype = DNA   length = 30
FEATURE                 Location/Qualifiers
source                  1..30
                        mol_type = other DNA
                        organism = synthetic construct
```

-continued

```
SEQUENCE: 10
acgttggatg ctgatggctt gaccaatagg                                         30

SEQ ID NO: 11             moltype = DNA   length = 30
FEATURE                   Location/Qualifiers
source                    1..30
                          mol_type = other DNA
                          organism = synthetic construct
SEQUENCE: 11
acgttggatg tactaccttc tcttctgctg                                         30

SEQ ID NO: 12             moltype = DNA   length = 24
FEATURE                   Location/Qualifiers
source                    1..24
                          mol_type = other DNA
                          organism = synthetic construct
SEQUENCE: 12
tatgtcttga ccaataggtt gacc                                               24

SEQ ID NO: 13             moltype = DNA   length = 30
FEATURE                   Location/Qualifiers
source                    1..30
                          mol_type = other DNA
                          organism = synthetic construct
SEQUENCE: 13
acgttggatg tactaccttc tcttctgctg                                         30

SEQ ID NO: 14             moltype = DNA   length = 30
FEATURE                   Location/Qualifiers
source                    1..30
                          mol_type = other DNA
                          organism = synthetic construct
SEQUENCE: 14
acgttggatg ctgatggctt gaccaatagg                                         30

SEQ ID NO: 15             moltype = DNA   length = 24
FEATURE                   Location/Qualifiers
source                    1..24
                          mol_type = other DNA
                          organism = synthetic construct
SEQUENCE: 15
ggattcactt tacaatttgc aaaa                                               24

SEQ ID NO: 16             moltype = DNA   length = 30
FEATURE                   Location/Qualifiers
source                    1..30
                          mol_type = other DNA
                          organism = synthetic construct
SEQUENCE: 16
acgttggatg gaaaatgtaa cccaggacgc                                         30

SEQ ID NO: 17             moltype = DNA   length = 30
FEATURE                   Location/Qualifiers
source                    1..30
                          mol_type = other DNA
                          organism = synthetic construct
SEQUENCE: 17
acgttggatg actgtgaagt tgtcagcctc                                         30

SEQ ID NO: 18             moltype = DNA   length = 18
FEATURE                   Location/Qualifiers
source                    1..18
                          mol_type = other DNA
                          organism = synthetic construct
SEQUENCE: 18
tcttcgaacc ttcactat                                                      18

SEQ ID NO: 19             moltype = DNA   length = 29
FEATURE                   Location/Qualifiers
source                    1..29
                          mol_type = other DNA
                          organism = synthetic construct
SEQUENCE: 19
acgttggatg ggactcactc acctgtacg                                          29

SEQ ID NO: 20             moltype = DNA   length = 30
FEATURE                   Location/Qualifiers
source                    1..30
                          mol_type = other DNA
```

-continued

```
                               organism = synthetic construct
SEQUENCE: 20
acgttggatg aggcacagaa gtttacagac                                    30

SEQ ID NO: 21          moltype = DNA   length = 23
FEATURE                Location/Qualifiers
source                 1..23
                       mol_type = other DNA
                       organism = synthetic construct
SEQUENCE: 21
acttctgttc atcatcactt cct                                           23

SEQ ID NO: 22          moltype = DNA   length = 30
FEATURE                Location/Qualifiers
source                 1..30
                       mol_type = other DNA
                       organism = synthetic construct
SEQUENCE: 22
acgttggatg tgcaatacct ggcttttctc                                    30

SEQ ID NO: 23          moltype = DNA   length = 30
FEATURE                Location/Qualifiers
source                 1..30
                       mol_type = other DNA
                       organism = synthetic construct
SEQUENCE: 23
acgttggatg tatggactac actggaggag                                    30

SEQ ID NO: 24          moltype = DNA   length = 22
FEATURE                Location/Qualifiers
source                 1..22
                       mol_type = other DNA
                       organism = synthetic construct
SEQUENCE: 24
cctctctcaa caaaaggtgg aa                                            22

SEQ ID NO: 25          moltype = DNA   length = 30
FEATURE                Location/Qualifiers
source                 1..30
                       mol_type = other DNA
                       organism = synthetic construct
SEQUENCE: 25
acgttggatg caactgtggt agtaacaggg                                    30

SEQ ID NO: 26          moltype = DNA   length = 30
FEATURE                Location/Qualifiers
source                 1..30
                       mol_type = other DNA
                       organism = synthetic construct
SEQUENCE: 26
acgttggatg ccaagtcaga actttgagag                                    30

SEQ ID NO: 27          moltype = DNA   length = 26
FEATURE                Location/Qualifiers
source                 1..26
                       mol_type = other DNA
                       organism = synthetic construct
SEQUENCE: 27
gatccaaaat ggatccctat agcccc                                        26

SEQ ID NO: 28          moltype = DNA   length = 35
FEATURE                Location/Qualifiers
source                 1..35
                       mol_type = other DNA
                       organism = synthetic construct
SEQUENCE: 28
acgttggatg ggaacaaaat caaattagca acagc                              35

SEQ ID NO: 29          moltype = DNA   length = 33
FEATURE                Location/Qualifiers
source                 1..33
                       mol_type = other DNA
                       organism = synthetic construct
SEQUENCE: 29
acgttggatg ttttaatgac taacagctgc aaa                                33

SEQ ID NO: 30          moltype = DNA   length = 27
FEATURE                Location/Qualifiers
source                 1..27
```

-continued

```
                            mol_type = other DNA
                            organism = synthetic construct
SEQUENCE: 30
ggaagacaaa cctcattaag ccaaaga                                      27

SEQ ID NO: 31              moltype = DNA   length = 30
FEATURE                    Location/Qualifiers
source                     1..30
                           mol_type = other DNA
                           organism = synthetic construct
SEQUENCE: 31
acgttggatg tctttgggct cctgtcttac                                   30

SEQ ID NO: 32              moltype = DNA   length = 29
FEATURE                    Location/Qualifiers
source                     1..29
                           mol_type = other DNA
                           organism = synthetic construct
SEQUENCE: 32
acgttggatg cagagccctt gtcgctgag                                    29

SEQ ID NO: 33              moltype = DNA   length = 26
FEATURE                    Location/Qualifiers
source                     1..26
                           mol_type = other DNA
                           organism = synthetic construct
SEQUENCE: 33
ggcgcctgtc ttacaggccc tgcctc                                       26

SEQ ID NO: 34              moltype = DNA   length = 30
FEATURE                    Location/Qualifiers
source                     1..30
                           mol_type = other DNA
                           organism = synthetic construct
SEQUENCE: 34
acgttggatg ttagccagac tgagcttctc                                   30

SEQ ID NO: 35              moltype = DNA   length = 30
FEATURE                    Location/Qualifiers
source                     1..30
                           mol_type = other DNA
                           organism = synthetic construct
SEQUENCE: 35
acgttggatg aactccaaga gctctacctg                                   30

SEQ ID NO: 36              moltype = DNA   length = 15
FEATURE                    Location/Qualifiers
source                     1..15
                           mol_type = other DNA
                           organism = synthetic construct
SEQUENCE: 36
agcttgggtg tgggc                                                   15

SEQ ID NO: 37              moltype = DNA   length = 30
FEATURE                    Location/Qualifiers
source                     1..30
                           mol_type = other DNA
                           organism = synthetic construct
SEQUENCE: 37
acgttggatg gaagatctgt ctgcgatccc                                   30

SEQ ID NO: 38              moltype = DNA   length = 30
FEATURE                    Location/Qualifiers
source                     1..30
                           mol_type = other DNA
                           organism = synthetic construct
SEQUENCE: 38
acgttggatg tgggcctgac cactcctttg                                   30

SEQ ID NO: 39              moltype = DNA   length = 21
FEATURE                    Location/Qualifiers
source                     1..21
                           mol_type = other DNA
                           organism = synthetic construct
SEQUENCE: 39
ttactggggg aggggctggg g                                            21

SEQ ID NO: 40              moltype = DNA   length = 30
FEATURE                    Location/Qualifiers
```

-continued

```
source                   1..30
                         mol_type = other DNA
                         organism = synthetic construct
SEQUENCE: 40
acgttggatg aaatgccccg aagccaatcc                                    30

SEQ ID NO: 41            moltype = DNA   length = 30
FEATURE                  Location/Qualifiers
source                   1..30
                         mol_type = other DNA
                         organism = synthetic construct
SEQUENCE: 41
acgttggatg tgaaggatga tctgtggagc                                    30

SEQ ID NO: 42            moltype = DNA   length = 18
FEATURE                  Location/Qualifiers
source                   1..18
                         mol_type = other DNA
                         organism = synthetic construct
SEQUENCE: 42
aggttactgg tgagcttt                                                 18

SEQ ID NO: 43            moltype = DNA   length = 30
FEATURE                  Location/Qualifiers
source                   1..30
                         mol_type = other DNA
                         organism = synthetic construct
SEQUENCE: 43
acgttggatg agacgtgctc ttggtaggtg                                    30

SEQ ID NO: 44            moltype = DNA   length = 34
FEATURE                  Location/Qualifiers
source                   1..34
                         mol_type = other DNA
                         organism = synthetic construct
SEQUENCE: 44
acgttggatg ccaaatgcaa gttaaattac cagt                               34

SEQ ID NO: 45            moltype = DNA   length = 25
FEATURE                  Location/Qualifiers
source                   1..25
                         mol_type = other DNA
                         organism = synthetic construct
SEQUENCE: 45
cctagtctac ctgtttacta tcaaa                                         25

SEQ ID NO: 46            moltype = DNA   length = 30
FEATURE                  Location/Qualifiers
source                   1..30
                         mol_type = other DNA
                         organism = synthetic construct
SEQUENCE: 46
acgttggatg cagacacatt gaccacagag                                    30

SEQ ID NO: 47            moltype = DNA   length = 30
FEATURE                  Location/Qualifiers
source                   1..30
                         mol_type = other DNA
                         organism = synthetic construct
SEQUENCE: 47
acgttggatg tgctcagagg aggactatcg                                    30

SEQ ID NO: 48            moltype = DNA   length = 25
FEATURE                  Location/Qualifiers
source                   1..25
                         mol_type = other DNA
                         organism = synthetic construct
SEQUENCE: 48
tggtagcagg acgaatgcag ccccc                                         25

SEQ ID NO: 49            moltype = DNA   length = 30
FEATURE                  Location/Qualifiers
source                   1..30
                         mol_type = other DNA
                         organism = synthetic construct
SEQUENCE: 49
acgttggatg ttctttccat ccaggtgagc                                    30

SEQ ID NO: 50            moltype = DNA   length = 30
```

-continued

```
FEATURE                 Location/Qualifiers
source                  1..30
                        mol_type = other DNA
                        organism = synthetic construct
SEQUENCE: 50
acgttggatg cacgggcttt atggtaaagg                                    30

SEQ ID NO: 51           moltype = DNA   length = 15
FEATURE                 Location/Qualifiers
source                  1..15
                        mol_type = other DNA
                        organism = synthetic construct
SEQUENCE: 51
aaggtgcgag gctgt                                                    15

SEQ ID NO: 52           moltype = DNA   length = 30
FEATURE                 Location/Qualifiers
source                  1..30
                        mol_type = other DNA
                        organism = synthetic construct
SEQUENCE: 52
acgttggatg gctctttcac tgactcaatc                                    30

SEQ ID NO: 53           moltype = DNA   length = 30
FEATURE                 Location/Qualifiers
source                  1..30
                        mol_type = other DNA
                        organism = synthetic construct
SEQUENCE: 53
acgttggatg gagtgtaaga agtttgaccg                                    30

SEQ ID NO: 54           moltype = DNA   length = 20
FEATURE                 Location/Qualifiers
source                  1..20
                        mol_type = other DNA
                        organism = synthetic construct
SEQUENCE: 54
ccctgactca atctcgtcac                                               20

SEQ ID NO: 55           moltype = DNA   length = 30
FEATURE                 Location/Qualifiers
source                  1..30
                        mol_type = other DNA
                        organism = synthetic construct
SEQUENCE: 55
acgttggatg tgggcctgac cactcctttg                                    30

SEQ ID NO: 56           moltype = DNA   length = 30
FEATURE                 Location/Qualifiers
source                  1..30
                        mol_type = other DNA
                        organism = synthetic construct
SEQUENCE: 56
acgttggatg gaagatctgt ctgcgatccc                                    30

SEQ ID NO: 57           moltype = DNA   length = 16
FEATURE                 Location/Qualifiers
source                  1..16
                        mol_type = other DNA
                        organism = synthetic construct
SEQUENCE: 57
tcctttgccc ccccag                                                   16

SEQ ID NO: 58           moltype = DNA   length = 30
FEATURE                 Location/Qualifiers
source                  1..30
                        mol_type = other DNA
                        organism = synthetic construct
SEQUENCE: 58
acgttggatg tctttgggct cctgtcttac                                    30

SEQ ID NO: 59           moltype = DNA   length = 29
FEATURE                 Location/Qualifiers
source                  1..29
                        mol_type = other DNA
                        organism = synthetic construct
SEQUENCE: 59
acgttggatg cagagccctt gtcgctgag                                     29
```

-continued

```
SEQ ID NO: 60          moltype = DNA   length = 20
FEATURE                Location/Qualifiers
source                 1..20
                       mol_type = other DNA
                       organism = synthetic construct
SEQUENCE: 60
tttcacagtg agtgaggccc                                              20

SEQ ID NO: 61          moltype = DNA   length = 30
FEATURE                Location/Qualifiers
source                 1..30
                       mol_type = other DNA
                       organism = synthetic construct
SEQUENCE: 61
acgttggatg ccttcagaga atgtgtggag                                   30

SEQ ID NO: 62          moltype = DNA   length = 30
FEATURE                Location/Qualifiers
source                 1..30
                       mol_type = other DNA
                       organism = synthetic construct
SEQUENCE: 62
acgttggatg gctctttcac tgactcaatc                                   30

SEQ ID NO: 63          moltype = DNA   length = 28
FEATURE                Location/Qualifiers
source                 1..28
                       mol_type = other DNA
                       organism = synthetic construct
SEQUENCE: 63
tccccacatg acgaaaatac ctgcaacc                                     28

SEQ ID NO: 64          moltype = DNA   length = 30
FEATURE                Location/Qualifiers
source                 1..30
                       mol_type = other DNA
                       organism = synthetic construct
SEQUENCE: 64
acgttggatg agcttactgc tcctgctgct                                   30

SEQ ID NO: 65          moltype = DNA   length = 29
FEATURE                Location/Qualifiers
source                 1..29
                       mol_type = other DNA
                       organism = synthetic construct
SEQUENCE: 65
acgttggatg ttgtgtcgac agggaaggc                                    29

SEQ ID NO: 66          moltype = DNA   length = 15
FEATURE                Location/Qualifiers
source                 1..15
                       mol_type = other DNA
                       organism = synthetic construct
SEQUENCE: 66
cgctcgtgga ctgcg                                                   15

SEQ ID NO: 67          moltype = DNA   length = 30
FEATURE                Location/Qualifiers
source                 1..30
                       mol_type = other DNA
                       organism = synthetic construct
SEQUENCE: 67
acgttggatg accctttatt gtcagcaacc                                   30

SEQ ID NO: 68          moltype = DNA   length = 30
FEATURE                Location/Qualifiers
source                 1..30
                       mol_type = other DNA
                       organism = synthetic construct
SEQUENCE: 68
acgttggatg ccagtgttgt atgcactttc                                   30

SEQ ID NO: 69          moltype = DNA   length = 23
FEATURE                Location/Qualifiers
source                 1..23
                       mol_type = other DNA
                       organism = synthetic construct
SEQUENCE: 69
caaaaggtta acattttcag taa                                          23
```

```
SEQ ID NO: 70            moltype = DNA  length = 29
FEATURE                  Location/Qualifiers
source                   1..29
                         mol_type = other DNA
                         organism = synthetic construct
SEQUENCE: 70
acgttggatg gacacctgtg agaagtgcc                                      29

SEQ ID NO: 71            moltype = DNA  length = 30
FEATURE                  Location/Qualifiers
source                   1..30
                         mol_type = other DNA
                         organism = synthetic construct
SEQUENCE: 71
acgttggatg acctcccagc ctcccggctc                                     30

SEQ ID NO: 72            moltype = DNA  length = 17
FEATURE                  Location/Qualifiers
source                   1..17
                         mol_type = other DNA
                         organism = synthetic construct
SEQUENCE: 72
atgcctgcac ctttaag                                                   17

SEQ ID NO: 73            moltype = DNA  length = 33
FEATURE                  Location/Qualifiers
source                   1..33
                         mol_type = other DNA
                         organism = synthetic construct
SEQUENCE: 73
acgttggatg tcagttcttg gttttgtgat gtt                                 33

SEQ ID NO: 74            moltype = DNA  length = 30
FEATURE                  Location/Qualifiers
source                   1..30
                         mol_type = other DNA
                         organism = synthetic construct
SEQUENCE: 74
acgttggatg cacaaaacca gtagccaccc                                     30

SEQ ID NO: 75            moltype = DNA  length = 28
FEATURE                  Location/Qualifiers
source                   1..28
                         mol_type = other DNA
                         organism = synthetic construct
SEQUENCE: 75
gtttatattt attatcttga cttcagtt                                       28

SEQ ID NO: 76            moltype = DNA  length = 30
FEATURE                  Location/Qualifiers
source                   1..30
                         mol_type = other DNA
                         organism = synthetic construct
SEQUENCE: 76
acgttggatg tgaaggatga tctgtggagc                                     30

SEQ ID NO: 77            moltype = DNA  length = 30
FEATURE                  Location/Qualifiers
source                   1..30
                         mol_type = other DNA
                         organism = synthetic construct
SEQUENCE: 77
acgttggatg aaatgccccg aagccaatcc                                     30

SEQ ID NO: 78            moltype = DNA  length = 19
FEATURE                  Location/Qualifiers
source                   1..19
                         mol_type = other DNA
                         organism = synthetic construct
SEQUENCE: 78
ccccataccg agctggcca                                                 19

SEQ ID NO: 79            moltype = DNA  length = 30
FEATURE                  Location/Qualifiers
source                   1..30
                         mol_type = other DNA
                         organism = synthetic construct
SEQUENCE: 79
```

-continued

```
acgttggatg gtatgaagac cacctgcttg                                 30

SEQ ID NO: 80           moltype = DNA   length = 30
FEATURE                 Location/Qualifiers
source                  1..30
                        mol_type = other DNA
                        organism = synthetic construct
SEQUENCE: 80
acgttggatg gacacactct gcttcttcac                                 30

SEQ ID NO: 81           moltype = DNA   length = 25
FEATURE                 Location/Qualifiers
source                  1..25
                        mol_type = other DNA
                        organism = synthetic construct
SEQUENCE: 81
atgtgtggct acaaacacgt gctga                                      25

SEQ ID NO: 82           moltype = DNA   length = 30
FEATURE                 Location/Qualifiers
source                  1..30
                        mol_type = other DNA
                        organism = synthetic construct
SEQUENCE: 82
acgttggatg gtgcctgcag aagaatatgg                                 30

SEQ ID NO: 83           moltype = DNA   length = 30
FEATURE                 Location/Qualifiers
source                  1..30
                        mol_type = other DNA
                        organism = synthetic construct
SEQUENCE: 83
acgttggatg agtcaaaagg gatgttcctg                                 30

SEQ ID NO: 84           moltype = DNA   length = 21
FEATURE                 Location/Qualifiers
source                  1..21
                        mol_type = other DNA
                        organism = synthetic construct
SEQUENCE: 84
cgagcacatc atttatatac a                                          21

SEQ ID NO: 85           moltype = DNA   length = 30
FEATURE                 Location/Qualifiers
source                  1..30
                        mol_type = other DNA
                        organism = synthetic construct
SEQUENCE: 85
acgttggatg aaatgccccg aagccaatcc                                 30

SEQ ID NO: 86           moltype = DNA   length = 30
FEATURE                 Location/Qualifiers
source                  1..30
                        mol_type = other DNA
                        organism = synthetic construct
SEQUENCE: 86
acgttggatg tgaaggatga tctgtggagc                                 30

SEQ ID NO: 87           moltype = DNA   length = 24
FEATURE                 Location/Qualifiers
source                  1..24
                        mol_type = other DNA
                        organism = synthetic construct
SEQUENCE: 87
ctgagcatcc agaacctggg tacc                                       24

SEQ ID NO: 88           moltype = DNA   length = 30
FEATURE                 Location/Qualifiers
source                  1..30
                        mol_type = other DNA
                        organism = synthetic construct
SEQUENCE: 88
acgttggatg caccttagtc ccctctttc                                  30

SEQ ID NO: 89           moltype = DNA   length = 30
FEATURE                 Location/Qualifiers
source                  1..30
                        mol_type = other DNA
                        organism = synthetic construct
```

-continued

```
SEQUENCE: 89
acgttggatg cattatctgc cccaactagg                                        30

SEQ ID NO: 90          moltype = DNA   length = 22
FEATURE                Location/Qualifiers
source                 1..22
                       mol_type = other DNA
                       organism = synthetic construct
SEQUENCE: 90
tcacgcctct ttccccacag ga                                                22

SEQ ID NO: 91          moltype = DNA   length = 30
FEATURE                Location/Qualifiers
source                 1..30
                       mol_type = other DNA
                       organism = synthetic construct
SEQUENCE: 91
acgttggatg ccttcagaga atgtgtggag                                        30

SEQ ID NO: 92          moltype = DNA   length = 30
FEATURE                Location/Qualifiers
source                 1..30
                       mol_type = other DNA
                       organism = synthetic construct
SEQUENCE: 92
acgttggatg cactgactca atctcgtcac                                        30

SEQ ID NO: 93          moltype = DNA   length = 15
FEATURE                Location/Qualifiers
source                 1..15
                       mol_type = other DNA
                       organism = synthetic construct
SEQUENCE: 93
ggagccctac atgac                                                        15

SEQ ID NO: 94          moltype = DNA   length = 30
FEATURE                Location/Qualifiers
source                 1..30
                       mol_type = other DNA
                       organism = synthetic construct
SEQUENCE: 94
acgttggatg actgcgcttt tgctccctac                                        30

SEQ ID NO: 95          moltype = DNA   length = 30
FEATURE                Location/Qualifiers
source                 1..30
                       mol_type = other DNA
                       organism = synthetic construct
SEQUENCE: 95
acgttggatg tgacccctcc tccttgtctc                                        30

SEQ ID NO: 96          moltype = DNA   length = 20
FEATURE                Location/Qualifiers
source                 1..20
                       mol_type = other DNA
                       organism = synthetic construct
SEQUENCE: 96
gggacgcttc acagtaacgc                                                   20

SEQ ID NO: 97          moltype = DNA   length = 30
FEATURE                Location/Qualifiers
source                 1..30
                       mol_type = other DNA
                       organism = synthetic construct
SEQUENCE: 97
acgttggatg ccttcagaga atgtgtggag                                        30

SEQ ID NO: 98          moltype = DNA   length = 30
FEATURE                Location/Qualifiers
source                 1..30
                       mol_type = other DNA
                       organism = synthetic construct
SEQUENCE: 98
acgttggatg cactgactca atctcgtcac                                        30

SEQ ID NO: 99          moltype = DNA   length = 19
FEATURE                Location/Qualifiers
source                 1..19
                       mol_type = other DNA
```

-continued

```
                                    organism = synthetic construct
SEQUENCE: 99
ggagtgtaag aagtttgac                                            19

SEQ ID NO: 100         moltype = DNA   length = 30
FEATURE                Location/Qualifiers
source                 1..30
                       mol_type = other DNA
                       organism = synthetic construct
SEQUENCE: 100
acgttggatg agatccttta aggcccatgc                                30

SEQ ID NO: 101         moltype = DNA   length = 30
FEATURE                Location/Qualifiers
source                 1..30
                       mol_type = other DNA
                       organism = synthetic construct
SEQUENCE: 101
acgttggatg cagctactgg tgcaagattc                                30

SEQ ID NO: 102         moltype = DNA   length = 20
FEATURE                Location/Qualifiers
source                 1..20
                       mol_type = other DNA
                       organism = synthetic construct
SEQUENCE: 102
tggtctgagg taggacacag                                           20

SEQ ID NO: 103         moltype = DNA   length = 30
FEATURE                Location/Qualifiers
source                 1..30
                       mol_type = other DNA
                       organism = synthetic construct
SEQUENCE: 103
acgttggatg acagggaagg gtgtgatatg                                30

SEQ ID NO: 104         moltype = DNA   length = 30
FEATURE                Location/Qualifiers
source                 1..30
                       mol_type = other DNA
                       organism = synthetic construct
SEQUENCE: 104
acgttggatg tccagacagt acagctaacg                                30

SEQ ID NO: 105         moltype = DNA   length = 17
FEATURE                Location/Qualifiers
source                 1..17
                       mol_type = other DNA
                       organism = synthetic construct
SEQUENCE: 105
ggtgtgatat gctcacc                                              17

SEQ ID NO: 106         moltype = DNA   length = 30
FEATURE                Location/Qualifiers
source                 1..30
                       mol_type = other DNA
                       organism = synthetic construct
SEQUENCE: 106
acgttggatg actactgcaa ctgtaccacg                                30

SEQ ID NO: 107         moltype = DNA   length = 30
FEATURE                Location/Qualifiers
source                 1..30
                       mol_type = other DNA
                       organism = synthetic construct
SEQUENCE: 107
acgttggatg tggatacaga cacagctgcc                                30

SEQ ID NO: 108         moltype = DNA   length = 23
FEATURE                Location/Qualifiers
source                 1..23
                       mol_type = other DNA
                       organism = synthetic construct
SEQUENCE: 108
atgatgtgca gcggccgcgg caa                                       23

SEQ ID NO: 109         moltype = DNA   length = 30
FEATURE                Location/Qualifiers
source                 1..30
```

```
                         mol_type = other DNA
                         organism = synthetic construct
SEQUENCE: 109
acgttggatg tgggcctgac cactcctttg                                    30

SEQ ID NO: 110          moltype = DNA   length = 30
FEATURE                 Location/Qualifiers
source                  1..30
                         mol_type = other DNA
                         organism = synthetic construct
SEQUENCE: 110
acgttggatg gaagatctgt ctgcgatccc                                    30

SEQ ID NO: 111          moltype = DNA   length = 16
FEATURE                 Location/Qualifiers
source                  1..16
                         mol_type = other DNA
                         organism = synthetic construct
SEQUENCE: 111
ccaggtggac tggggg                                                   16

SEQ ID NO: 112          moltype = DNA   length = 30
FEATURE                 Location/Qualifiers
source                  1..30
                         mol_type = other DNA
                         organism = synthetic construct
SEQUENCE: 112
acgttggatg gccagaatcc aaacagcaag                                    30

SEQ ID NO: 113          moltype = DNA   length = 30
FEATURE                 Location/Qualifiers
source                  1..30
                         mol_type = other DNA
                         organism = synthetic construct
SEQUENCE: 113
acgttggatg tgaatgccat ctcccttctc                                    30

SEQ ID NO: 114          moltype = DNA   length = 16
FEATURE                 Location/Qualifiers
source                  1..16
                         mol_type = other DNA
                         organism = synthetic construct
SEQUENCE: 114
aattgtgctg ctggac                                                   16

SEQ ID NO: 115          moltype = DNA   length = 30
FEATURE                 Location/Qualifiers
source                  1..30
                         mol_type = other DNA
                         organism = synthetic construct
SEQUENCE: 115
acgttggatg tttgtctgtc tgttgcaggg                                    30

SEQ ID NO: 116          moltype = DNA   length = 30
FEATURE                 Location/Qualifiers
source                  1..30
                         mol_type = other DNA
                         organism = synthetic construct
SEQUENCE: 116
acgttggatg tccttacctc atcagagcac                                    30

SEQ ID NO: 117          moltype = DNA   length = 18
FEATURE                 Location/Qualifiers
source                  1..18
                         mol_type = other DNA
                         organism = synthetic construct
SEQUENCE: 117
ggcccaacat ctgtacca                                                 18

SEQ ID NO: 118          moltype = DNA   length = 30
FEATURE                 Location/Qualifiers
source                  1..30
                         mol_type = other DNA
                         organism = synthetic construct
SEQUENCE: 118
acgttggatg tgggactgtg aatggtcttc                                    30

SEQ ID NO: 119          moltype = DNA   length = 30
FEATURE                 Location/Qualifiers
```

```
source                   1..30
                         mol_type = other DNA
                         organism = synthetic construct
SEQUENCE: 119
acgttggatg gctgtatatc caggatgtag                                      30

SEQ ID NO: 120          moltype = DNA   length = 23
FEATURE                 Location/Qualifiers
source                   1..23
                         mol_type = other DNA
                         organism = synthetic construct
SEQUENCE: 120
ctcagcatcc accttccggg aca                                             23

SEQ ID NO: 121          moltype = DNA   length = 29
FEATURE                 Location/Qualifiers
source                   1..29
                         mol_type = other DNA
                         organism = synthetic construct
SEQUENCE: 121
acgttggatg agctggtagc ctgtcagcc                                       29

SEQ ID NO: 122          moltype = DNA   length = 30
FEATURE                 Location/Qualifiers
source                   1..30
                         mol_type = other DNA
                         organism = synthetic construct
SEQUENCE: 122
acgttggatg tgactgcagc ctcacctatc                                      30

SEQ ID NO: 123          moltype = DNA   length = 27
FEATURE                 Location/Qualifiers
source                   1..27
                         mol_type = other DNA
                         organism = synthetic construct
SEQUENCE: 123
agctggtagc ctgtcagccg gcccagc                                         27

SEQ ID NO: 124          moltype = DNA   length = 30
FEATURE                 Location/Qualifiers
source                   1..30
                         mol_type = other DNA
                         organism = synthetic construct
SEQUENCE: 124
acgttggatg tgaaggatga tctgtggagc                                      30

SEQ ID NO: 125          moltype = DNA   length = 30
FEATURE                 Location/Qualifiers
source                   1..30
                         mol_type = other DNA
                         organism = synthetic construct
SEQUENCE: 125
acgttggatg aaatgccccg aagccaatcc                                      30

SEQ ID NO: 126          moltype = DNA   length = 17
FEATURE                 Location/Qualifiers
source                   1..17
                         mol_type = other DNA
                         organism = synthetic construct
SEQUENCE: 126
gaagccaatc cgcaggt                                                    17

SEQ ID NO: 127          moltype = DNA   length = 30
FEATURE                 Location/Qualifiers
source                   1..30
                         mol_type = other DNA
                         organism = synthetic construct
SEQUENCE: 127
acgttggatg ttgcagcgat ggctattagg                                      30

SEQ ID NO: 128          moltype = DNA   length = 30
FEATURE                 Location/Qualifiers
source                   1..30
                         mol_type = other DNA
                         organism = synthetic construct
SEQUENCE: 128
acgttggatg cttcaaggac agcctgatcg                                      30

SEQ ID NO: 129          moltype = DNA   length = 17
```

-continued

```
FEATURE              Location/Qualifiers
source               1..17
                     mol_type = other DNA
                     organism = synthetic construct
SEQUENCE: 129
agcaggcaca gtcacaa                                                17

SEQ ID NO: 130       moltype = DNA   length = 30
FEATURE              Location/Qualifiers
source               1..30
                     mol_type = other DNA
                     organism = synthetic construct
SEQUENCE: 130
acgttggatg ccaggtcact caagtcagtc                                  30

SEQ ID NO: 131       moltype = DNA   length = 30
FEATURE              Location/Qualifiers
source               1..30
                     mol_type = other DNA
                     organism = synthetic construct
SEQUENCE: 131
acgttggatg tccaccttgt gctctatgcc                                  30

SEQ ID NO: 132       moltype = DNA   length = 25
FEATURE              Location/Qualifiers
source               1..25
                     mol_type = other DNA
                     organism = synthetic construct
SEQUENCE: 132
ggtcagtccc cagaggattg cactc                                       25

SEQ ID NO: 133       moltype = DNA   length = 30
FEATURE              Location/Qualifiers
source               1..30
                     mol_type = other DNA
                     organism = synthetic construct
SEQUENCE: 133
acgttggatg atcccagtgt gagtgctcag                                  30

SEQ ID NO: 134       moltype = DNA   length = 30
FEATURE              Location/Qualifiers
source               1..30
                     mol_type = other DNA
                     organism = synthetic construct
SEQUENCE: 134
acgttggatg attgaccaca gaggcactcg                                  30

SEQ ID NO: 135       moltype = DNA   length = 24
FEATURE              Location/Qualifiers
source               1..24
                     mol_type = other DNA
                     organism = synthetic construct
SEQUENCE: 135
gtgagtgctc agaggaggac tatc                                        24

SEQ ID NO: 136       moltype = DNA   length = 30
FEATURE              Location/Qualifiers
source               1..30
                     mol_type = other DNA
                     organism = synthetic construct
SEQUENCE: 136
acgttggatg ttgtctggca cctgtactct                                  30

SEQ ID NO: 137       moltype = DNA   length = 33
FEATURE              Location/Qualifiers
source               1..33
                     mol_type = other DNA
                     organism = synthetic construct
SEQUENCE: 137
acgttggatg cccctactca atatttgatt tac                              33

SEQ ID NO: 138       moltype = DNA   length = 24
FEATURE              Location/Qualifiers
source               1..24
                     mol_type = other DNA
                     organism = synthetic construct
SEQUENCE: 138
gggagcagtg gtttcacaat gaga                                        24
```

-continued

```
SEQ ID NO: 139          moltype = DNA   length = 33
FEATURE                 Location/Qualifiers
source                  1..33
                        mol_type = other DNA
                        organism = synthetic construct
SEQUENCE: 139
acgttggatg cccctactca atatttgatt tac                               33

SEQ ID NO: 140          moltype = DNA   length = 30
FEATURE                 Location/Qualifiers
source                  1..30
                        mol_type = other DNA
                        organism = synthetic construct
SEQUENCE: 140
acgttggatg ttgtctggca cctgtactct                                   30

SEQ ID NO: 141          moltype = DNA   length = 20
FEATURE                 Location/Qualifiers
source                  1..20
                        mol_type = other DNA
                        organism = synthetic construct
SEQUENCE: 141
ggcggtcgtt gactgtggca                                              20

SEQ ID NO: 142          moltype = DNA   length = 30
FEATURE                 Location/Qualifiers
source                  1..30
                        mol_type = other DNA
                        organism = synthetic construct
SEQUENCE: 142
acgttggatg taacgaggtt gttgcagaag                                   30

SEQ ID NO: 143          moltype = DNA   length = 30
FEATURE                 Location/Qualifiers
source                  1..30
                        mol_type = other DNA
                        organism = synthetic construct
SEQUENCE: 143
acgttggatg tgagcctggt gctctccaag                                   30

SEQ ID NO: 144          moltype = DNA   length = 25
FEATURE                 Location/Qualifiers
source                  1..25
                        mol_type = other DNA
                        organism = synthetic construct
SEQUENCE: 144
aaggggttgt tgcagaagtc ctcct                                        25

SEQ ID NO: 145          moltype = DNA   length = 30
FEATURE                 Location/Qualifiers
source                  1..30
                        mol_type = other DNA
                        organism = synthetic construct
SEQUENCE: 145
acgttggatg tgagcctggt gctctccaag                                   30

SEQ ID NO: 146          moltype = DNA   length = 30
FEATURE                 Location/Qualifiers
source                  1..30
                        mol_type = other DNA
                        organism = synthetic construct
SEQUENCE: 146
acgttggatg taacgaggtt gttgcagaag                                   30

SEQ ID NO: 147          moltype = DNA   length = 19
FEATURE                 Location/Qualifiers
source                  1..19
                        mol_type = other DNA
                        organism = synthetic construct
SEQUENCE: 147
gcatgagccc cgcgtcact                                               19

SEQ ID NO: 148          moltype = DNA   length = 30
FEATURE                 Location/Qualifiers
source                  1..30
                        mol_type = other DNA
                        organism = synthetic construct
SEQUENCE: 148
acgttggatg gtggcagtgt actagacttg                                   30
```

-continued

```
SEQ ID NO: 149          moltype = DNA   length = 30
FEATURE                 Location/Qualifiers
source                  1..30
                        mol_type = other DNA
                        organism = synthetic construct
SEQUENCE: 149
acgttggatg tgactcacag ggtttgctgg                                    30

SEQ ID NO: 150          moltype = DNA   length = 20
FEATURE                 Location/Qualifiers
source                  1..20
                        mol_type = other DNA
                        organism = synthetic construct
SEQUENCE: 150
ggaagggagt ggctgaggtg                                               20

SEQ ID NO: 151          moltype = DNA   length = 30
FEATURE                 Location/Qualifiers
source                  1..30
                        mol_type = other DNA
                        organism = synthetic construct
SEQUENCE: 151
acgttggatg tgactcacag ggtttgctgg                                    30

SEQ ID NO: 152          moltype = DNA   length = 30
FEATURE                 Location/Qualifiers
source                  1..30
                        mol_type = other DNA
                        organism = synthetic construct
SEQUENCE: 152
acgttggatg gtggcagtgt actagacttg                                    30

SEQ ID NO: 153          moltype = DNA   length = 15
FEATURE                 Location/Qualifiers
source                  1..15
                        mol_type = other DNA
                        organism = synthetic construct
SEQUENCE: 153
gggcagtcac catct                                                    15

SEQ ID NO: 154          moltype = DNA   length = 30
FEATURE                 Location/Qualifiers
source                  1..30
                        mol_type = other DNA
                        organism = synthetic construct
SEQUENCE: 154
acgttggatg ctctaccagt gcgactacag                                    30

SEQ ID NO: 155          moltype = DNA   length = 30
FEATURE                 Location/Qualifiers
source                  1..30
                        mol_type = other DNA
                        organism = synthetic construct
SEQUENCE: 155
acgttggatg aagtccctat gtgttcacag                                    30

SEQ ID NO: 156          moltype = DNA   length = 19
FEATURE                 Location/Qualifiers
source                  1..19
                        mol_type = other DNA
                        organism = synthetic construct
SEQUENCE: 156
tgctcatgcg agcccatcc                                                19

SEQ ID NO: 157          moltype = DNA   length = 30
FEATURE                 Location/Qualifiers
source                  1..30
                        mol_type = other DNA
                        organism = synthetic construct
SEQUENCE: 157
acgttggatg cctcagttct gatattcccc                                    30

SEQ ID NO: 158          moltype = DNA   length = 30
FEATURE                 Location/Qualifiers
source                  1..30
                        mol_type = other DNA
                        organism = synthetic construct
SEQUENCE: 158
```

-continued

```
acgttggatg gctggcaaaa gcagttagac                                          30

SEQ ID NO: 159           moltype = DNA   length = 17
FEATURE                  Location/Qualifiers
source                   1..17
                         mol_type = other DNA
                         organism = synthetic construct
SEQUENCE: 159
tatccccac agatcca                                                         17

SEQ ID NO: 160           moltype = DNA   length = 28
FEATURE                  Location/Qualifiers
source                   1..28
                         mol_type = other DNA
                         organism = synthetic construct
SEQUENCE: 160
acgttggatg agcttactgc tcctgctg                                            28

SEQ ID NO: 161           moltype = DNA   length = 29
FEATURE                  Location/Qualifiers
source                   1..29
                         mol_type = other DNA
                         organism = synthetic construct
SEQUENCE: 161
acgttggatg ttgtgtcgac agggaaggc                                           29

SEQ ID NO: 162           moltype = DNA   length = 30
FEATURE                  Location/Qualifiers
source                   1..30
                         mol_type = other DNA
                         organism = synthetic construct
SEQUENCE: 162
acgttggatg agcttactgc tcctgctgct                                          30

SEQ ID NO: 163           moltype = DNA   length = 29
FEATURE                  Location/Qualifiers
source                   1..29
                         mol_type = other DNA
                         organism = synthetic construct
SEQUENCE: 163
acgttggatg gttgtgtcga cagggaagg                                           29

SEQ ID NO: 164           moltype = DNA   length = 31
FEATURE                  Location/Qualifiers
source                   1..31
                         mol_type = other DNA
                         organism = synthetic construct
SEQUENCE: 164
acgttggatg cctgtactct ccactgtcgt t                                        31

SEQ ID NO: 165           moltype = DNA   length = 30
FEATURE                  Location/Qualifiers
source                   1..30
                         mol_type = other DNA
                         organism = synthetic construct
SEQUENCE: 165
acgttggatg cttgggaatg gcagtgtaga                                          30

SEQ ID NO: 166           moltype = DNA   length = 31
FEATURE                  Location/Qualifiers
source                   1..31
                         mol_type = other DNA
                         organism = synthetic construct
SEQUENCE: 166
acgttggatg cctgtactct ccactgtcgt t                                        31

SEQ ID NO: 167           moltype = DNA   length = 30
FEATURE                  Location/Qualifiers
source                   1..30
                         mol_type = other DNA
                         organism = synthetic construct
SEQUENCE: 167
acgttggatg aagcacgctg taccattgag                                          30

SEQ ID NO: 168           moltype = DNA   length = 31
FEATURE                  Location/Qualifiers
source                   1..31
                         mol_type = other DNA
                         organism = synthetic construct
```

-continued

```
SEQUENCE: 168
acgttggatg cctgtactct ccactgtcgt t                                    31

SEQ ID NO: 169          moltype = DNA   length = 30
FEATURE                 Location/Qualifiers
source                  1..30
                        mol_type = other DNA
                        organism = synthetic construct
SEQUENCE: 169
acgttggatg ctcaatggta cagcgtgctt                                      30

SEQ ID NO: 170          moltype = DNA   length = 30
FEATURE                 Location/Qualifiers
source                  1..30
                        mol_type = other DNA
                        organism = synthetic construct
SEQUENCE: 170
acgttggatg ggaagagtct acctgtttac                                      30

SEQ ID NO: 171          moltype = DNA   length = 33
FEATURE                 Location/Qualifiers
source                  1..33
                        mol_type = other DNA
                        organism = synthetic construct
SEQUENCE: 171
acgttggatg gaaggaagag tctacctgtt tac                                  33

SEQ ID NO: 172          moltype = DNA   length = 30
FEATURE                 Location/Qualifiers
source                  1..30
                        mol_type = other DNA
                        organism = synthetic construct
SEQUENCE: 172
acgttggatg gtaaaccata ctatctgtgc                                      30

SEQ ID NO: 173          moltype = DNA   length = 35
FEATURE                 Location/Qualifiers
source                  1..35
                        mol_type = other DNA
                        organism = synthetic construct
SEQUENCE: 173
acgttggatg gaaatgtaaa ccatactatc tgtgc                                35

SEQ ID NO: 174          moltype = DNA   length = 30
FEATURE                 Location/Qualifiers
source                  1..30
                        mol_type = other DNA
                        organism = synthetic construct
SEQUENCE: 174
acgttggatg caaaatgtat cagttcttgg                                      30

SEQ ID NO: 175          moltype = DNA   length = 36
FEATURE                 Location/Qualifiers
source                  1..36
                        mol_type = other DNA
                        organism = synthetic construct
SEQUENCE: 175
acgttggatg ttatttcaaa atgtatcagt tcttgg                               36

SEQ ID NO: 176          moltype = DNA   length = 30
FEATURE                 Location/Qualifiers
source                  1..30
                        mol_type = other DNA
                        organism = synthetic construct
SEQUENCE: 176
acgttggatg agccacccaa gaagtgatag                                      30

SEQ ID NO: 177          moltype = DNA   length = 24
FEATURE                 Location/Qualifiers
source                  1..24
                        mol_type = other DNA
                        organism = synthetic construct
SEQUENCE: 177
acgttggatg agccaccctg atag                                            24

SEQ ID NO: 178          moltype = DNA   length = 30
FEATURE                 Location/Qualifiers
source                  1..30
                        mol_type = other DNA
```

-continued

```
                         organism = synthetic construct
SEQUENCE: 178
acgttggatg cagctgcaaa tacaaacctc                                    30

SEQ ID NO: 179          moltype = DNA  length = 35
FEATURE                 Location/Qualifiers
source                  1..35
                        mol_type = other DNA
                        organism = synthetic construct
SEQUENCE: 179
acgttggatg aattagcaac agcaactaat ttatg                              35

SEQ ID NO: 180          moltype = DNA  length = 30
FEATURE                 Location/Qualifiers
source                  1..30
                        mol_type = other DNA
                        organism = synthetic construct
SEQUENCE: 180
acgttggatg gcaacagcaa ctaatttatg                                    30

SEQ ID NO: 181          moltype = DNA  length = 31
FEATURE                 Location/Qualifiers
source                  1..31
                        mol_type = other DNA
                        organism = synthetic construct
SEQUENCE: 181
acgttggatg acagctgcaa atacaaacct c                                  31
```

KIT FOR GENOTYPING OF PLATELET AND NEUTROPHIL ANTIGENS AND GLYCOPROTEINS

The present application claims the priority of the Chinese application with the application number of 2022100980235 applied on 2022 Jan. 26, and all the recorded contents serve as a part of the present invention.

REFERENCE TO AN ELECTRONIC SEQUENCE LISTING

The contents of the electronic sequence listing (2023-01-19-SequenceListing.xml; Size: 161,707 bytes; and Date of Creation: Jan. 9, 2023) is herein incorporated by reference in its entirety.

TECHNICAL FIELD

The present invention relates to the field of biomedicine, in particular to a mass spectrometry-based method and a kit for genotyping of platelet and neutrophil antigens and glycoproteins.

BACKGROUND

Surface antigens of platelets and neutrophils as well as some membrane glycoproteins are closely related to blood transfusion and clinic. Inconsistency of platelet and neutrophil antigen phenotypes between fetuses and mothers or between donors and recipients of blood transfusion, etc. can lead to iso-immunization, and then lead to a series of clinical problems such as platelet transfusion refractoriness, which are important in blood transfusion, transplantation, maternal health care, etc. By conducting accurate genotyping on clinically significant platelet and neutrophil antigens or membrane glycoproteins, corresponding phenotypes can be predicted so that effective clinical measures can be taken.

There are complex and diverse antigen types on surfaces of platelets, mainly including two main types of platelet-associated antigens (antigens that also exist on surfaces of other cells and tissues, such as HLA, ABO antigens, etc.) and platelet-specific antigens (HPA). At present, 35 HPA systems have been found, namely HPA1-35w. HPA iso-antibodies produced by immunization can lead to neonatal iso-immune thrombocytopenia, platelet transfusion refractoriness, post-transfusion purpura, etc.

CD36 is a widely expressed glycoprotein in the human body, and it is expressed in all human platelets, macrophages, endothelial cells, etc. People with CD36 expression deletion may produce anti-CD36 antibodies by immunization in ways such as blood transfusion and pregnancy, which may then lead to neonatal iso-immune thrombocytopenia and even early fetal death, platelet transfusion refractoriness, post-transfusion purpura, transfusion-related acute lung injury and other clinical symptoms. Transfusion of blood components containing anti-CD36 antibodies in patients with a normal CD36 phenotype may also lead to adverse transfusion reactions, resulting in thrombocytopenia and even threatening to life. Since the proportion of people with CD36 expression deletion in Asian populations including China is significantly higher than that in Caucasian populations, the production of anti-CD36 iso-antibodies is an important risk factor for immune-mediated thrombocytopenia in Chinese populations. In addition to the normal phenotype, there are different types of CD36 antigen abnormalities such as type I deletion, type II deletion and weak expression according to different degrees of CD36 deletion and different intensities of expression. Among them, type I deletion refers to the absence of CD36 expression on both platelets and monocytes. Type II deletion refers to that there is no CD36 expression on the surfaces of the platelets, but there is normal expression of CD36 on the surfaces of the monocytes and the macrophages. Weak expression of CD36 refers to that there is expression of CD36 on the surfaces of the platelets, but an expression quantity thereof is significantly lower than a normal level.

Neutrophil antigens (HNA) are a group of glycoproteins expressed on the surfaces of human neutrophils and play an important role in iso-immunization and auto-immunization Certain HNAs also exist on other cells and tissues. At present, 5 HNA systems have been found, namely HNA 1-5. Due to the polymorphism of the HNA, corresponding antibodies can lead to neonatal iso-immune neutropenia, auto-immune neutropenia, febrile transfusion reaction, transfusion-related acute lung injury, etc.

In view of the important clinical significance of platelet and neutrophil antigens and CD36 proteins, accurate typing and identification of these antigens and proteins are necessary. Existing detection methods mainly distinguish different antigen expressions at a protein level or a gene level. Due to the insufficiency or lack of commercial specific antibodies, it is impossible to comprehensively type these antigens or proteins. Therefore, under the premise that the genetic background of the above antigens or proteins is becoming more and more clear at present, genotyping has become a better detection means. To meet clinical needs, it is necessary to establish a high-throughput, rapid and accurate genotyping method for clinically significant platelet and neutrophil antigens and proteins. A nucleic acid mass spectrometry technology has the characteristics of simultaneous detection of SNP and In/Del, short detection time, high detection throughput of a single amplification tube, accuracy and specificity, etc., which can meet the detection needs of the above antigens and proteins.

CN111455027A and CN110172502 provide mass spectrometric detection methods and kits for platelet antigen genotyping, but CN110172502 can only be used for detecting up to 21 HPA sites (HPA1-21w), and CN111455027A can only be used for detecting up to 29 HPA sites (HPA1-29w), so it is difficult to perform one-time typing and detection of all current known HPA sites of platelets (HPA1-35w). Meanwhile, CN111455027A and CN110172502 do not show the corresponding relationship between detection results and phenotypes.

Due to the existence of homologous sequences, rich GC and other problems, up to now, genotyping methods and products for simultaneous detection of 35 platelet antigen genetic sites and simultaneous detection of CD36 glycoproteins by a mass spectrometry technology cannot be achieved, and there are also no genotyping methods and products that can simultaneously detect multiple polymorphic sites such as CD36 glycoproteins, neutrophil antigens and platelet antigens.

SUMMARY OF THE INVENTION

Due to the problems that genes of platelet-specific antigens, CD36 glycoproteins and neutrophil antigens have genes with very high homology to the surrounding, moreover, sequences where some SNP sites are located are rich in GC, etc., and genes where some SNP sites are located have highly homologous sequences, resulting in that when the SNP sites of these genes are detected simultaneously based on mass spectrometry, the situations are prone to occurring that some sites do not have peaks and are not detected, or it is easy to amplify to homologous sequences to generate erroneous results, etc., and there is a problem that it is difficult to detect all sites one time.

In view of the problems in the prior art, the present invention provides a mass spectrometry-based method and a kit for genotyping of platelet and neutrophil antigens and glycoproteins, which are used for genotyping of platelet-specific antigens, CD36 glycoproteins and neutrophil antigens. By designing a primer combination and improving amplification reaction conditions, 35 platelet-specific antigen polymorphic sites, 10 CD36 polymorphic sites and 8 neutrophil antigen polymorphic sites can be simultaneously detected one time in one reaction (an amplification reaction and an extension reaction), which have the characteristics of high specificity and sensitivity, and fast and high throughput. The present invention can be used in clinic, scientific research, platelet donor routine screening, etc.

In the present invention, by screening a large number of primer combinations and adjusting an annealing temperature and a primer concentration, finally, 35 platelet-specific antigen polymorphic sites, 10 CD36 polymorphic sites and 8 neutrophil antigen polymorphic sites can be simultaneously detected one time. Moreover, high specificity and sensitivity and fast and high throughput are achieved.

On the one hand, the present invention provides a kit that comprises a mulit-amplificatiion tube that includes primer combination for CD36 genotyping. The primer combination includes amplification primers and extension primers. The amplification primers include forward primers and reverse primers. Sequences and the extension primers of the primer combination are shown in Table 1.

TABLE 1

| List of a primer combination for CD36 genotyping | | | | |
|---|---|---|---|---|
| Detected genes | SNP sites | Forward primers | Reverse primers | Extension primers |
| CD36 (1) | rs550565800 | SEQ ID NO: 1 | SEQ ID NO: 2 | SEQ ID NO: 3 |
| CD36 (2) | rs75326924 | SEQ ID NO: 4 | SEQ ID NO: 5 | SEQ ID NO: 6 |
| CD36 (3) | rs572295823 | SEQ ID NO: 7 | SEQ ID NO: 8 | SEQ ID NO: 9 |
| CD36 (4) | rs201355711 | SEQ ID NO: 10 | SEQ ID NO: 11 | SEQ ID NO: 12 |
| CD36 (5) | rs148910227 | SEQ ID NO: 13 | SEQ ID NO: 14 | SEQ ID NO: 15 |
| CD36 (6) | rs201765331 | SEQ ID NO: 16 | SEQ ID NO: 17 | SEQ ID NO: 18 |
| CD36 (7) | rs545489204 | SEQ ID NO: 19 | SEQ ID NO: 20 | SEQ ID NO: 21 |
| CD36 (8) | rs142186404 | SEQ ID NO: 22 | SEQ ID NO: 23 | SEQ ID NO: 24 |
| CD36 (9) | rs201759307 | SEQ ID NO: 25 | SEQ ID NO: 26 | SEQ ID NO: 27 |
| CD36 (10) | rs767892046 | SEQ ID NO: 28 | SEQ ID NO: 29 | SEQ ID NO: 30 |

The primer combination for CD36 genotyping can simultaneously detect 10 polymorphic sites of CD36 at one time.

On the other hand, the present invention provides a mulit-amplificatiion tube that includes a primer combination for platelet antigens. The primer combination includes amplification primers and extension primers. The amplification primers include forward primers and reverse primers. Sequences of the primer combination are shown in Table 2.

The primer combination for platelet antigens can simultaneously detect 35 SNP sites of platelet antigens at one time.

TABLE 2

| List of a primer combination for genotyping of platelet antigens | | | | |
|---|---|---|---|---|
| Detected systems | SNP sites | Forward primers | Reverse primers | Extension primers |
| HPA-1 | rs5918 | SEQ ID NO: 31 | SEQ ID NO: 32 | SEQ ID NO: 33 |
| HPA-2 | rs6065 | SEQ ID NO: 34 | SEQ ID NO: 35 | SEQ ID NO: 36 |
| HPA-3 | rs5911 | SEQ ID NO: 37 | SEQ ID NO: 38 | SEQ ID NO: 39 |
| HPA-4 | rs5917 | SEQ ID NO: 40 | SEQ ID NO: 41 | SEQ ID NO: 42 |
| HPA-5 | rs1801106 | SEQ ID NO: 43 | SEQ ID NO: 44 | SEQ ID NO: 45 |
| HPA-6w | rs13306487 | SEQ ID NO: 46 | SEQ ID NO: 47 | SEQ ID NO: 48 |
| HPA-7w | rs121918448 | SEQ ID NO: 49 | SEQ ID NO: 50 | SEQ ID NO: 51 |
| HPA-8w | rs151219882 | SEQ ID NO: 52 | SEQ ID NO: 53 | SEQ ID NO: 54 |
| HPA-9w | rs74988902 | SEQ ID NO: 55 | SEQ ID NO: 56 | SEQ ID NO: 57 |
| HPA-10w | rs200358667 | SEQ ID NO: 58 | SEQ ID NO: 59 | SEQ ID NO: 60 |
| HPA-11w | rs377302275 | SEQ ID NO: 61 | SEQ ID NO: 62 | SEQ ID NO: 63 |
| HPA-12w | rs375285857 | SEQ ID NO: 64 | SEQ ID NO: 65 | SEQ ID NO: 66 |
| HPA-13w | rs79932422 | SEQ ID NO: 67 | SEQ ID NO: 68 | SEQ ID NO: 69 |
| HPA-14w | HPA-14w | SEQ ID NO: 70 | SEQ ID NO: 71 | SEQ ID NO: 72 |
| HPA-15 | rs10455097 | SEQ ID NO: 73 | SEQ ID NO: 74 | SEQ ID NO: 75 |
| HPA-16w | rs74708909 | SEQ ID NO: 76 | SEQ ID NO: 77 | SEQ ID NO: 78 |
| HPA-17w | rs770992614 | SEQ ID NO: 79 | SEQ ID NO: 80 | SEQ ID NO: 81 |
| HPA-18w | rs267606593 | SEQ ID NO: 82 | SEQ ID NO: 83 | SEQ ID NO: 84 |
| HPA-19w | rs80115510 | SEQ ID NO: 85 | SEQ ID NO: 86 | SEQ ID NO: 87 |

TABLE 2-continued

| Detected systems | SNP sites | Forward primers | Reverse primers | Extension primers |
|---|---|---|---|---|
| HPA-20w | rs78299130 | SEQ ID NO: 88 | SEQ ID NO: 89 | SEQ ID NO: 90 |
| HPA-21w | rs70940817 | SEQ ID NO: 91 | SEQ ID NO: 92 | SEQ ID NO: 93 |
| HPA-22w | rs142811900 | SEQ ID NO: 94 | SEQ ID NO: 95 | SEQ ID NO: 96 |
| HPA-23w | rs139166528 | SEQ ID NO: 97 | SEQ ID NO: 98 | SEQ ID NO: 99 |
| HPA-24w | rs281864910 | SEQ ID NO: 100 | SEQ ID NO: 101 | SEQ ID NO: 102 |
| HPA-25w | rs771035051 | SEQ ID NO: 103 | SEQ ID NO: 104 | SEQ ID NO: 105 |
| HPA-26w | rs1156382155 | SEQ ID NO: 106 | SEQ ID NO: 107 | SEQ ID NO: 108 |
| HPA-27w | rs 149468422 | SEQ ID NO: 109 | SEQ ID NO: 110 | SEQ ID NO: 111 |
| HPA-28w | rs368953599 | SEQ ID NO: 112 | SEQ ID NO: 113 | SEQ ID NO: 114 |
| HPA-29w | rs544276300 | SEQ ID NO: 115 | SEQ ID NO: 116 | SEQ ID NO: 117 |
| HPA-30w | rs377753373 | SEQ ID NO: 118 | SEQ ID NO: 119 | SEQ ID NO: 120 |
| HPA-31w | rs202229101 | SEQ ID NO: 121 | SEQ ID NO: 122 | SEQ ID NO: 123 |
| HPA-32w | rs879083862 | SEQ ID NO: 124 | SEQ ID NO: 125 | SEQ ID NO: 126 |
| HPA-33w | rs1555572829 | SEQ ID NO: 127 | SEQ ID NO: 128 | SEQ ID NO: 129 |
| HPA-34w | rs777748046 | SEQ ID NO: 130 | SEQ ID NO: 131 | SEQ ID NO: 132 |
| HPA-35w | rs779974422 | SEQ ID NO: 133 | SEQ ID NO: 134 | SEQ ID NO: 135 |

On the other hand, the present invention provides a primer combination for platelet antigen and CD36 genotyping. The primer combination includes amplification primers and extension primers. The amplification primers include forward primers and reverse primers. Sequences of the primer combination are shown in Table 3. The primer combination for platelet antigens (35 SNP sites) and CD36(10) can be simultaneously detected at one time.

TABLE 3

| Detected genes/systems | SNP sites | Forward primers | Reverse primers | Extension primers |
|---|---|---|---|---|
| CD36 (1) | rs550565800 | SEQ ID NO: 1 | SEQ ID NO: 2 | SEQ ID NO: 3 |
| CD36 (2) | rs75326924 | SEQ ID NO: 4 | SEQ ID NO: 5 | SEQ ID NO: 6 |
| CD36 (3) | rs572295823 | SEQ ID NO: 7 | SEQ ID NO: 8 | SEQ ID NO: 9 |
| CD36 (4) | rs201355711 | SEQ ID NO: 10 | SEQ ID NO: 11 | SEQ ID NO: 12 |
| CD36 (5) | rs148910227 | SEQ ID NO: 13 | SEQ ID NO: 14 | SEQ ID NO: 15 |
| CD36 (6) | rs201765331 | SEQ ID NO: 16 | SEQ ID NO: 17 | SEQ ID NO: 18 |
| CD36 (7) | rs545489204 | SEQ ID NO: 19 | SEQ ID NO: 20 | SEQ ID NO: 21 |
| CD36 (8) | rs142186404 | SEQ ID NO: 22 | SEQ ID NO: 23 | SEQ ID NO: 24 |
| CD36 (9) | rs201759307 | SEQ ID NO: 25 | SEQ ID NO: 26 | SEQ ID NO: 27 |
| CD36 (10) | rs767892046 | SEQ ID NO: 28 | SEQ ID NO: 29 | SEQ ID NO: 30 |
| HPA-1 | rs5918 | SEQ ID NO: 31 | SEQ ID NO: 32 | SEQ ID NO: 33 |
| HPA-2 | rs6065 | SEQ ID NO: 34 | SEQ ID NO: 35 | SEQ ID NO: 36 |
| HPA-3 | rs5911 | SEQ ID NO: 37 | SEQ ID NO: 38 | SEQ ID NO: 39 |
| HPA-4 | rs5917 | SEQ ID NO: 40 | SEQ ID NO: 41 | SEQ ID NO: 42 |
| HPA-5 | rs1801106 | SEQ ID NO: 43 | SEQ ID NO: 44 | SEQ ID NO: 45 |
| HPA-6w | rs13306487 | SEQ ID NO: 46 | SEQ ID NO: 47 | SEQ ID NO: 48 |
| HPA-7w | rs121918448 | SEQ ID NO: 49 | SEQ ID NO: 50 | SEQ ID NO: 51 |

TABLE 3-continued

List of a primer combination for platelet antigen and CD36 genotyping

| Detected genes/systems | SNP sites | Forward primers | Reverse primers | Extension primers |
|---|---|---|---|---|
| HPA-8w | rs151219882 | SEQ ID NO: 52 | SEQ ID NO: 53 | SEQ ID NO: 54 |
| HPA-9w | rs74988902 | SEQ ID NO: 55 | SEQ ID NO: 56 | SEQ ID NO: 57 |
| HPA-10w | rs2003 58667 | SEQ ID NO: 58 | SEQ ID NO: 59 | SEQ ID NO: 60 |
| HPA-11w | rs377302275 | SEQ ID NO: 61 | SEQ ID NO: 62 | SEQ ID NO: 63 |
| HPA-12w | rs375285857 | SEQ ID NO: 64 | SEQ ID NO: 65 | SEQ ID NO: 66 |
| HPA-13w | rs79932422 | SEQ ID NO: 67 | SEQ ID NO: 68 | SEQ ID NO: 69 |
| HPA-14w | HPA-14w | SEQ ID NO: 70 | SEQ ID NO: 71 | SEQ ID NO: 72 |
| HPA-15 | rs10455097 | SEQ ID NO: 73 | SEQ ID NO: 74 | SEQ ID NO: 75 |
| HPA-16w | rs74708909 | SEQ ID NO: 76 | SEQ ID NO: 77 | SEQ ID NO: 78 |
| HPA-17w | rs770992614 | SEQ ID NO: 79 | SEQ ID NO: 80 | SEQ ID NO: 81 |
| HPA-18w | rs267606593 | SEQ ID NO: 82 | SEQ ID NO: 83 | SEQ ID NO: 84 |
| HPA-19w | rs80115510 | SEQ ID NO: 85 | SEQ ID NO: 86 | SEQ ID NO: 87 |
| HPA-20w | rs78299130 | SEQ ID NO: 88 | SEQ ID NO: 89 | SEQ ID NO: 90 |
| HPA-21w | rs70940817 | SEQ ID NO: 91 | SEQ ID NO: 92 | SEQ ID NO: 93 |
| HPA-22w | rs142811900 | SEQ ID NO: 94 | SEQ ID NO: 95 | SEQ ID NO: 96 |
| HPA-23w | rs139166528 | SEQ ID NO: 97 | SEQ ID NO: 98 | SEQ ID NO: 99 |
| HPA-24w | rs281864910 | SEQ ID NO: 100 | SEQ ID NO: 101 | SEQ ID NO: 102 |
| HPA-25w | rs771035051 | SEQ ID NO: 103 | SEQ ID NO: 104 | SEQ ID NO: 105 |
| HPA-26w | rs1156382155 | SEQ ID NO: 106 | SEQ ID NO: 107 | SEQ ID NO: 108 |
| HPA-27w | rs149468422 | SEQ ID NO: 109 | SEQ ID NO: 110 | SEQ ID NO: 111 |
| HPA-28w | rs368953599 | SEQ ID NO: 112 | SEQ ID NO: 113 | SEQ ID NO: 114 |
| HPA-29w | rs544276300 | SEQ ID NO: 115 | SEQ ID NO: 116 | SEQ ID NO: 117 |
| HPA-30w | rs377753373 | SEQ ID NO: 118 | SEQ ID NO: 119 | SEQ ID NO: 120 |
| HPA-31w | rs202229101 | SEQ ID NO: 121 | SEQ ID NO: 122 | SEQ ID NO: 123 |
| HPA-32w | rs879083862 | SEQ ID NO: 124 | SEQ ID NO: 125 | SEQ ID NO: 126 |
| HPA-33w | rs1555572829 | SEQ ID NO: 127 | SEQ ID NO: 128 | SEQ ID NO: 129 |
| HPA-34w | rs777748046 | SEQ ID NO: 130 | SEQ ID NO: 131 | SEQ ID NO: 132 |
| HPA-35w | rs779974422 | SEQ ID NO: 133 | SEQ ID NO: 134 | SEQ ID NO: 135 |

The primer combination for platelet antigen and CD36 genotyping can simultaneously detect 35 polymorphic sites of platelet antigens and 10 polymorphic sites of CD36.

On yet another hand, the present invention provides a primer combination for neutrophil antigen and CD36 genotyping. The primer combination includes amplification primers and extension primers. The amplification primers include forward primers and reverse primers. Sequences of the primer combination are shown in Table 4.

TABLE 4

List of a primer combination for neutrophil antigen and CD36 genotyping

| Detected genes/sy stems | SNP sites | Forward primers | Reverse primers | Extension primers |
|---|---|---|---|---|
| CD36 (1) | rs550565800 | SEQ ID NO: 1 | SEQ ID NO: 2 | SEQ ID NO: 3 |
| CD36 (2) | rs75326924 | SEQ ID NO: 4 | SEQ ID NO: 5 | SEQ ID NO: 6 |
| CD36 (3) | rs572295823 | SEQ ID NO: 7 | SEQ ID NO: 8 | SEQ ID NO: 9 |
| CD36 (4) | rs201355711 | SEQ ID NO: 10 | SEQ ID NO: 11 | SEQ ID NO: 12 |
| CD36 (5) | rs148910227 | SEQ ID NO: 13 | SEQ ID NO: 14 | SEQ ID NO: 15 |
| CD36 (6) | rs201765331 | SEQ ID NO: 16 | SEQ ID NO: 17 | SEQ ID NO: 18 |
| CD36 (7) | rs545489204 | SEQ ID NO: 19 | SEQ ID NO: 20 | SEQ ID NO: 21 |
| CD36 (8) | rs142186404 | SEQ ID NO: 22 | SEQ ID NO: 23 | SEQ ID NO: 24 |
| CD36 (9) | rs201759307 | SEQ ID NO: 25 | SEQ ID NO: 26 | SEQ ID NO: 27 |
| CD36 (10) | rs767892046 | SEQ ID NO: 28 | SEQ ID NO: 29 | SEQ ID NO: 30 |
| HNA-1 (1) | rs448740 | SEQ ID NO: 136 | SEQ ID NO: 137 | SEQ ID NO: 138 |
| HNA-1 (2) | rs5030738 | SEQ ID NO: 139 | SEQ ID NO: 140 | SEQ ID NO: 141 |
| HNA-2 (1) | rs777225032 | SEQ ID NO: 142 | SEQ ID NO: 143 | SEQ ID NO: 144 |
| HNA-2 (2) | rs1230516223 | SEQ ID NO: 145 | SEQ ID NO: 146 | SEQ ID NO: 147 |
| HNA-3 (1) | rs147820753 | SEQ ID NO: 148 | SEQ ID NO: 149 | SEQ ID NO: 150 |
| HNA-3 (2) | rs2288904 | SEQ ID NO: 151 | SEQ ID NO: 152 | SEQ ID NO: 153 |
| HNA-4 | rs1143679 | SEQ ID NO: 154 | SEQ ID NO: 155 | SEQ ID NO: 156 |
| HNA-5 | rs2230433 | SEQ ID NO: 157 | SEQ ID NO: 158 | SEQ ID NO: 159 |

The primer combination for neutrophil antigen and CD36 genotyping can simultaneously detect 8 polymorphic sites of neutrophil antigens and 10 polymorphic sites of CD36.

On yet another hand, the present invention provides a primer combination for genotyping of platelet antigens and neutrophil antigens. The primer combination includes amplification primers and extension primers. The amplification primers include forward primers and reverse primers. Sequences of the primer combination are shown in Table 5.

TABLE 5

List of a primer combination for genotyping of platelet antigens and neutrophil antigens

| Detected systems | SNP sites | Forward primers | Reverse primers | Extension primers |
|---|---|---|---|---|
| HPA-1 | rs5918 | SEQ ID NO: 31 | SEQ ID NO: 32 | SEQ ID NO: 33 |
| HPA-2 | rs6065 | SEQ ID NO: 34 | SEQ ID NO: 35 | SEQ ID NO: 36 |
| HPA-3 | rs5911 | SEQ ID NO: 37 | SEQ ID NO: 38 | SEQ ID NO: 39 |
| HPA-4 | rs5917 | SEQ ID NO: 40 | SEQ ID NO: 41 | SEQ ID NO: 42 |
| HPA-5 | rs1801106 | SEQ ID NO: 43 | SEQ ID NO: 44 | SEQ ID NO: 45 |
| HPA-6w | rs13306487 | SEQ ID NO: 46 | SEQ ID NO: 47 | SEQ ID NO: 48 |
| HPA-7w | rs121918448 | SEQ ID NO: 49 | SEQ ID NO: 50 | SEQ ID NO: 51 |
| HPA-8w | rs151219882 | SEQ ID NO: 52 | SEQ ID NO: 53 | SEQ ID NO: 54 |
| HPA-9w | rs74988902 | SEQ ID NO: 55 | SEQ ID NO: 56 | SEQ ID NO: 57 |
| HPA-10w | rs200358667 | SEQ ID NO: 58 | SEQ ID NO: 59 | SEQ ID NO: 60 |
| HPA-11w | rs377302275 | SEQ ID NO: 61 | SEQ ID NO: 62 | SEQ ID NO: 63 |
| HPA-12w | rs375285857 | SEQ ID NO: 64 | SEQ ID NO: 65 | SEQ ID NO: 66 |
| HPA-13w | rs79932422 | SEQ ID NO: 67 | SEQ ID NO: 68 | SEQ ID NO: 69 |
| HPA-14w | HPA-14w | SEQ ID NO: 70 | SEQ ID NO: 71 | SEQ ID NO: 72 |
| HPA-15 | rs10455097 | SEQ ID NO: 73 | SEQ ID NO: 74 | SEQ ID NO: 75 |
| HPA-16w | rs74708909 | SEQ ID NO: 76 | SEQ ID NO: 77 | SEQ ID NO: 78 |
| HPA-17w | rs770992614 | SEQ ID NO: 79 | SEQ ID NO: 80 | SEQ ID NO: 81 |
| HPA-18w | rs267606593 | SEQ ID NO: 82 | SEQ ID NO: 83 | SEQ ID NO: 84 |
| HPA-19w | rs80115510 | SEQ ID NO: 85 | SEQ ID NO: 86 | SEQ ID NO: 87 |

TABLE 5-continued

| Detected systems | SNP sites | Forward primers | Reverse primers | Extension primers |
|---|---|---|---|---|
| | | List of a primer combination for genotyping of platelet antigens and neutrophil antigens | | |
| HPA-20w | rs78299130 | SEQ ID NO: 88 | SEQ ID NO: 89 | SEQ ID NO: 90 |
| HPA-21w | rs70940817 | SEQ ID NO: 91 | SEQ ID NO: 92 | SEQ ID NO: 93 |
| HPA-22w | rs142811900 | SEQ ID NO: 94 | SEQ ID NO: 95 | SEQ ID NO: 96 |
| HPA-23w | rs139166528 | SEQ ID NO: 97 | SEQ ID NO: 98 | SEQ ID NO: 99 |
| HPA-24w | rs281864910 | SEQ ID NO: 100 | SEQ ID NO: 101 | SEQ ID NO: 102 |
| HPA-25w | rs771035051 | SEQ ID NO: 103 | SEQ ID NO: 104 | SEQ ID NO: 105 |
| HPA-26w | rs1156382155 | SEQ ID NO: 106 | SEQ ID NO: 107 | SEQ ID NO: 108 |
| HPA-27w | rs149468422 | SEQ ID NO: 109 | SEQ ID NO: 110 | SEQ ID NO: 111 |
| HPA-28w | rs368953599 | SEQ ID NO: 112 | SEQ ID NO: 113 | SEQ ID NO: 114 |
| HPA-29w | rs544276300 | SEQ ID NO: 115 | SEQ ID NO: 116 | SEQ ID NO: 117 |
| HPA-30w | rs377753373 | SEQ ID NO: 118 | SEQ ID NO: 119 | SEQ ID NO: 120 |
| HPA-31w | rs202229101 | SEQ ID NO: 121 | SEQ ID NO: 122 | SEQ ID NO: 123 |
| HPA-32w | rs879083862 | SEQ ID NO: 124 | SEQ ID NO: 125 | SEQ ID NO: 126 |
| HPA-33w | rs1555572829 | SEQ ID NO: 127 | SEQ ID NO: 128 | SEQ ID NO: 129 |
| HPA-34w | rs777748046 | SEQ ID NO: 130 | SEQ ID NO: 131 | SEQ ID NO: 132 |
| HPA-35w | rs779974422 | SEQ ID NO: 133 | SEQ ID NO: 134 | SEQ ID NO: 135 |
| HNA-1 (1) | rs448740 | SEQ ID NO: 136 | SEQ ID NO: 137 | SEQ ID NO: 138 |
| HNA-1 (2) | rs5030738 | SEQ ID NO: 139 | SEQ ID NO: 140 | SEQ ID NO: 141 |
| HNA-2 (1) | rs777225032 | SEQ ID NO: 142 | SEQ ID NO: 143 | SEQ ID NO: 144 |
| HNA-2 (2) | rs1230516223 | SEQ ID NO: 145 | SEQ ID NO: 146 | SEQ ID NO: 147 |
| HNA-3 (1) | rs147820753 | SEQ ID NO: 148 | SEQ ID NO: 149 | SEQ ID NO: 150 |
| HNA-3 (2) | rs2288904 | SEQ ID NO: 151 | SEQ ID NO: 152 | SEQ ID NO: 153 |
| HNA-4 | rs1143679 | SEQ ID NO: 154 | SEQ ID NO: 155 | SEQ ID NO: 156 |
| HNA-5 | rs2230433 | SEQ ID NO: 157 | SEQ ID NO: 158 | SEQ ID NO: 159 |

The primer combination for genotyping of the platelet antigens and the neutrophil antigens can simultaneously detect 35 polymorphic sites of the platelet antigens and 8 polymorphic sites of the neutrophil antigens.

On yet another hand, the present invention provides a primer combination for genotyping of platelet antigens, neutrophil antigens and CD36. The primer combination includes amplification primers and extension primers. The amplification primers include forward primers and reverse primers. Sequences of the primer combination are shown in Table 6.

TABLE 6

| Detected genes/systems | SNP sites | Forward primers | Reverse primers | Extension primers |
|---|---|---|---|---|
| | | List of a primer combination for genotyping of platelet antigens, neutrophil antigens and CD36 | | |
| CD36 (1) | rs550565800 | SEQ ID NO: 1 | SEQ ID NO: 2 | SEQ ID NO: 3 |
| CD36 (2) | rs75326924 | SEQ ID NO: 4 | SEQ ID NO: 5 | SEQ ID NO: 6 |
| CD36 (3) | rs572295823 | SEQ ID NO: 7 | SEQ ID NO: 8 | SEQ ID NO: 9 |
| CD36 (4) | rs201355711 | SEQ ID NO: 10 | SEQ ID NO: 11 | SEQ ID NO: 12 |
| CD36 (5) | rs148910227 | SEQ ID NO: 13 | SEQ ID NO: 14 | SEQ ID NO: 15 |
| CD36 (6) | rs201765331 | SEQ ID NO: 16 | SEQ ID NO: 17 | SEQ ID NO: 18 |

TABLE 6-continued

List of a primer combination for genotyping of platelet antigens,
neutrophil antigens and CD36

| Detected genes/systems | SNP sites | Forward primers | Reverse primers | Extension primers |
|---|---|---|---|---|
| CD36 (7) | rs545489204 | SEQ ID NO: 19 | SEQ ID NO: 20 | SEQ ID NO: 21 |
| CD36 (8) | rs142186404 | SEQ ID NO: 22 | SEQ ID NO: 23 | SEQ ID NO: 24 |
| CD36 (9) | rs201759307 | SEQ ID NO: 25 | SEQ ID NO: 26 | SEQ ID NO: 27 |
| CD36 (10) | rs767892046 | SEQ ID NO: 28 | SEQ ID NO: 29 | SEQ ID NO: 30 |
| HPA-1 | rs5918 | SEQ ID NO: 31 | SEQ ID NO: 32 | SEQ ID NO: 33 |
| HPA-2 | rs6065 | SEQ ID NO: 34 | SEQ ID NO: 35 | SEQ ID NO: 36 |
| HPA-3 | rs5911 | SEQ ID NO: 37 | SEQ ID NO: 38 | SEQ ID NO: 39 |
| HPA-4 | rs5917 | SEQ ID NO: 40 | SEQ ID NO: 41 | SEQ ID NO: 42 |
| HPA-5 | rs1801106 | SEQ ID NO: 43 | SEQ ID NO: 44 | SEQ ID NO: 45 |
| HPA-6w | rs13306487 | SEQ ID NO: 46 | SEQ ID NO: 47 | SEQ ID NO: 48 |
| HPA-7w | rs121918448 | SEQ ID NO: 49 | SEQ ID NO: 50 | SEQ ID NO: 51 |
| HPA-8w | rs151219882 | SEQ ID NO: 52 | SEQ ID NO: 53 | SEQ ID NO: 54 |
| HPA-9w | rs74988902 | SEQ ID NO: 55 | SEQ ID NO: 56 | SEQ ID NO: 57 |
| HPA-10w | rs2003 58667 | SEQ ID NO: 58 | SEQ ID NO: 59 | SEQ ID NO: 60 |
| HPA-11w | rs377302275 | SEQ ID NO: 61 | SEQ ID NO: 62 | SEQ ID NO: 63 |
| HPA-12w | rs375285857 | SEQ ID NO: 64 | SEQ ID NO: 65 | SEQ ID NO: 66 |
| HPA-13w | rs79932422 | SEQ ID NO: 67 | SEQ ID NO: 68 | SEQ ID NO: 69 |
| HPA-14w | HPA-14w | SEQ ID NO: 70 | SEQ ID NO: 71 | SEQ ID NO: 72 |
| HPA-15 | rs10455097 | SEQ ID NO: 73 | SEQ ID NO: 74 | SEQ ID NO: 75 |
| HPA-16w | rs74708909 | SEQ ID NO: 76 | SEQ ID NO: 77 | SEQ ID NO: 78 |
| HPA-17w | rs770992614 | SEQ ID NO: 79 | SEQ ID NO: 80 | SEQ ID NO: 81 |
| HPA-18w | rs267606593 | SEQ ID NO: 82 | SEQ ID NO: 83 | SEQ ID NO: 84 |
| HPA-19w | rs80115510 | SEQ ID NO: 85 | SEQ ID NO: 86 | SEQ ID NO: 87 |
| HPA-20w | rs78299130 | SEQ ID NO: 88 | SEQ ID NO: 89 | SEQ ID NO: 90 |
| HPA-21w | rs70940817 | SEQ ID NO: 91 | SEQ ID NO: 92 | SEQ ID NO: 93 |
| HPA-22w | rs142811900 | SEQ ID NO: 94 | SEQ ID NO: 95 | SEQ ID NO: 96 |
| HPA-23w | rs139166528 | SEQ ID NO: 97 | SEQ ID NO: 98 | SEQ ID NO: 99 |
| HPA-24w | rs281864910 | SEQ ID NO: 100 | SEQ ID NO: 101 | SEQ ID NO: 102 |
| HPA-25w | rs771035051 | SEQ ID NO: 103 | SEQ ID NO: 104 | SEQ ID NO: 105 |
| HPA-26w | rs1156382155 | SEQ ID NO: 106 | SEQ ID NO: 107 | SEQ ID NO: 108 |
| HPA-27w | rs149468422 | SEQ ID NO: 109 | SEQ ID NO: 110 | SEQ ID NO: 111 |
| HPA-28w | rs368953599 | SEQ ID NO: 112 | SEQ ID NO: 113 | SEQ ID NO: 114 |
| HPA-29w | rs544276300 | SEQ ID NO: 115 | SEQ ID NO: 116 | SEQ ID NO: 117 |
| HPA-30w | rs377753373 | SEQ ID NO: 118 | SEQ ID NO: 119 | SEQ ID NO: 120 |
| HPA-31w | rs202229101 | SEQ ID NO: 121 | SEQ ID NO: 122 | SEQ ID NO: 123 |
| HPA-32w | rs879083862 | SEQ ID NO: 124 | SEQ ID NO: 125 | SEQ ID NO: 126 |

TABLE 6-continued

List of a primer combination for genotyping of platelet antigens,
neutrophil antigens and CD36

| Detected genes/systems | SNP sites | Forward primers | Reverse primers | Extension primers |
|---|---|---|---|---|
| HPA-33w | rs1555572829 | SEQ ID NO: 127 | SEQ ID NO: 128 | SEQ ID NO: 129 |
| HPA-34w | rs777748046 | SEQ ID NO: 130 | SEQ ID NO: 131 | SEQ ID NO: 132 |
| HPA-35w | rs779974422 | SEQ ID NO: 133 | SEQ ID NO: 134 | SEQ ID NO: 135 |
| HNA-1 (1) | rs448740 | SEQ ID NO: 136 | SEQ ID NO: 137 | SEQ ID NO: 138 |
| HNA-1 (2) | rs5030738 | SEQ ID NO: 139 | SEQ ID NO: 140 | SEQ ID NO: 141 |
| HNA-2 (1) | rs777225032 | SEQ ID NO: 142 | SEQ ID NO: 143 | SEQ ID NO: 144 |
| HNA-2 (2) | rs1230516223 | SEQ ID NO: 145 | SEQ ID NO: 146 | SEQ ID NO: 147 |
| HNA-3 (1) | rs147820753 | SEQ ID NO: 148 | SEQ ID NO: 149 | SEQ ID NO: 150 |
| HNA-3 (2) | rs2288904 | SEQ ID NO: 151 | SEQ ID NO: 152 | SEQ ID NO: 153 |
| HNA-4 | rs1143679 | SEQ ID NO: 154 | SEQ ID NO: 155 | SEQ ID NO: 156 |
| HNA-5 | rs2230433 | SEQ ID NO: 157 | SEQ ID NO: 158 | SEQ ID NO: 159 |

The primer combination for genotyping of the platelet antigens, the neutrophil antigens and the CD36 can simultaneously detect 35 polymorphic sites of the platelet antigens, 8 polymorphic sites of the neutrophil antigens and 10 polymorphic sites of the CD36 one time.

A sample of the present invention may be blood, or nucleic acids, such as DNA, extracted from the blood.

Information of the 10 polymorphic sites of the CD36, the 35 polymorphic sites of the platelet antigens and the 8 polymorphic sites of the neutrophil antigens of the present invention is shown in Table 7 respectively, in which, among sequences, sequences in parentheses are polymorphic sites.

Genotype and phenotype information of the 10 polymorphic sites of the CD36, the 35 polymorphic sites of the platelet antigens and 7 polymorphic sites of the neutrophil antigens of the present invention is shown in Table 7.

TABLE 7

Genotype and phenotype information

| Detected genes/ systems | SNP sites | Polymorphism | Correspondence between genotype and phenotype |
|---|---|---|---|
| CD36 (1) | rs550565800 | ATTGTGCCTATT > -, ATTGTGCCTATTGT GCCTATT | del/del: type I deletion, ATTGTGCCTATT/del: type II deletion, weak expression and normality, ATTGTGCCTATT/ATTGTGCCTATT: normality |
| CD36 (2) | rs75326924 | C > T | T/T: type I deletion, C/T: type II deletion and normality, C/C: normality |
| CD36 (3) | rs572295823 | CA > - | del/del: type I deletion CA/del: type I deletion, type II deletion, weak expression and normality, CA/CA: normality |
| CD36 (4) | rs201355711 | A > T, C | T/T: no reports A/T: type I deletion, type II deletion and weak expression, A/A: normality |
| CD36 (5) | rs148910227 | C > T,G | T/T: no reports, C/T: type II deletion, C/C: normality |
| CD36 (6) | rs201765331 | C > T,G | T/T: no reports, C/T: no reports, C/C: normality |
| CD36 (7) | rs545489204 | C > T | T/T: no reports, C/T: no reports C/C: normality |

TABLE 7-continued

| Detected genes/ systems | SNP sites | Polymorphism | Correspondence between genotype and phenotype |
|---|---|---|---|
| CD36 (8) | rs142186404 | T > C, G | C/C: type I deletion,<br>T/C: no reports,<br>T/T: normality |
| CD36 (9) | rs201759307 | T > C | C/C: no reports,<br>T/C: type II deletion and weak expression<br>T/T: normality |
| CD36 (10) | rs767892046 | ATATTAGTTTATAT<br>GTTCATAATTATTT<br>TCAACGTATATTA > - | del/del: no reports,<br>ins/del: type II deletion and weak expression<br>ins/ins: normality |
| Different SNP combinations of CD36 | | | rs550565800 del/rs75326924 T: type I deletion<br>rs550565800 del/rs572295823 del: type I deletion<br>rs572295823 del/rs201355711 T: type I deletion<br>rs572295823 del/rs148910227 T: deletion (type I/II unknown)<br>rs572295823 del/rs545489204 T: type I deletion |
| HPA-1 | rs5918 | T > C | HPA-1aa: T/T, HPA-1ab: T/C; HPA-1bb: C/C |
| HPA-2 | rs6065 | T > C | HPA-2aa: C/C, HPA-2ab: T/C; HPA-2bb: T/T |
| HPA-3 | rs5911 | A > C | HPA-3aa: A/A, HPA-3ab: A/C; HPA-3bb: C/C |
| HPA-4 | rs5917 | G > A | HPA-4aa: G/G, HPA-4ab: G/A; HPA-4bb: A/A |
| HPA-5 | rs1801106 | G > A | HPA-5aa: G/G, HPA-5ab: G/A; HPA-5bb: A/A |
| HPA-6w | rs13306487 | G > A | HPA-6aa: G/G, HPA-6abw: G/A; HPA-6bwbw: A/A |
| HPA-7w | rs121918448 | G > C | HPA-7aa: C/C, HPA-7abw: G/C; HPA-7bwbw: G/G |
| HPA-8w | rs151219882 | T > C | HPA-8aa: C/C, HPA-8abw: T/C; HPA-8bwbw: T/T |
| HPA-9w | rs74988902 | T > C | HPA-9aa: C/C, HPA-9abw: T/C; HPA-9bwbw: T/T |
| HPA-10w | rs200358667 | G > A | HPA-10aa: G/G, HPA-10abw: G/A; HPA-10bwbw: A/A |
| HPA-11w | rs377302275 | G > A | HPA-11aa: G/G, HPA-11abw: G/A; HPA-11bwbw: A/A |
| HPA-12w | rs375285857 | G > A | HPA-12aa: G/G, HPA-12abw: G/A; HPA-12bwbw: A/A |
| HPA-13w | rs79932422 | T > C | HPA-13aa: C/C, HPA-13abw: T/C; HPA-13bwbw: T/T |
| HPA-14w | HPA-14w (Santoso et al, Blood 99: 1205-14 (2002)) | AAG > - | HPA-14aa: AAG/AAG, HPA-14abw: AAG/del;<br>HPA-14bwbw: del/del |
| HPA-15 | rs10455097 | C > A | HPA-15aa: C/C, HPA-15ab: C/A; HPA-15bb: A/A |
| HPA-16w | rs74708909 | T > C | HPA-16aa: C/C, HPA-16abw: T/C; HPA-16bwbw: T/T |
| HPA-17w | rs770992614 | T > C | HPA-17aa: C/C, HPA-17abw: T/C; HPA-17bwbw: T/T |
| HPA-18w | rs267606593 | T > G | HPA-18aa: G/G, HPA-18abw: T/G; HPA-18bwbw: T/T |
| HPA-19w | rs80115510 | A > C | HPA-19aa: A/A, HPA-19abw: A/C; HPA-19bwbw: C/C |
| HPA-20w | rs78299130 | G > A | HPA-20aa: G/G, HPA-20abw: G/A; HPA-20bwbw: A/A |

TABLE 7-continued

Genotype and phenotype information

| Detected genes/ systems | SNP sites | Polymorphism | Correspondence between genotype and phenotype |
|---|---|---|---|
| HPA-21W | rs70940817 | G > A | HPA-21aa: G/G, HPA-21abw: G/A; HPA-21bwbw: A/A |
| HPA-22w | rs142811900 | T > G | HPA-22aa: T/T, HPA-22abw: T/G; HPA-22bwbw: G/G |
| HPA-23w | rs139166528 | T > C | HPA-23aa: C/C, HPA-23abw: T/C; HPA-23bwbw: T/T |
| HPA-24w | rs281864910 | T > C | HPA-24aa: C/C, HPA-24abw: T/C; HPA-24bwbw: T/T |
| HPA-25w | rs771035051 | T > C | HPA-25aa: C/C, HPA-25abw: T/C; HPA-25bwbw: T/T |
| HPA-26w | rs1156382155 | T > G | HPA-26aa: G/G, HPA-26abw: T/G; HPA-26bwbw: T/T |
| HPA-27w | rs149468422 | T > G | HPA-27aa: G/G, HPA-27abw: T/G; HPA-27bwbw: T/T |
| HPA-28w | rs368953599 | C > A | HPA-28aa: C/C, HPA-28abw: C/A; HPA-28bwbw: A/A |
| HPA-29w | rs544276300 | T > C | HPA-29aa: C/C, HPA-29abw: T/C; HPA-29bwbw: T/T |
| HPA-30w | rs377753373 | G > C | HPA-30aa: G/G, HPA-30abw: G/C; HPA-30bwbw: C/C |
| HPA-31W | rs202229101 | C > T | HPA-31aa: C/C, HPA-31abw: C/T; HPA-31bwbw: T/T |
| HPA-32w | rs879083862 | A > G | HPA-32aa: A/A, HPA-32abw: A/G; HPA-32bwbw: G/G |
| HPA-33w | rs1555572829 | A > G | HPA-33aa: A/A, HPA-33abw: A/G; HPA-33bwbw: G/G |
| HPA-34w | rs777748046 | C > T | HPA-34aa: C/C, HPA-34abw: C/T; HPA-34bwbw: T/T |
| HPA-35w | rs779974422 | G > A | HPA-35aa: G/G, HPA-35abw: G/A; HPA-35bwbw: A/A |
| HNA-1 (1) | rs448740 | T > A, C | rs448740 AA, rs5030738 CC: HNA-1a<br>rs448740 GG, rs5030738 CC: HNA-1b<br>rs448740 GG, rs5030738 AA: HNA-1bc |
| HNA-1 (2) | rs5030738 | G > A, T | rs448740 AG, rs5030738 CC: HNA-1ab<br>rs448740 GG, rs5030738 CA: HNA-1bc<br>rs448740 AG, rs5030738 CA: HNA-1abc |
| HNA-2 (1) | rs777225032 | C > T | rs777225032 CC, rs1230516223 GG: HNA-2<br>rs777225032 CC, rs1230516223 TT: HNA-2 null |
| HNA-2 (2) | rs1230516223 | G > A, T | rs777225032 TT, rs1230516223 GG: HNA-2 null<br>rs777225032 TT, rs1230516223 TT: HNA-2 null<br>rs777225032 CT, rs1230516223 GG: HNA-2<br>rs777225032 CT, rs1230516223 TT: HNA-2 null<br>rs777225032 CT, rs1230516223 GT: HNA-2 null<br>rs777225032 CC, rs1230516223 GT: HNA-2<br>rs777225032 GT, rs1230516223 TT: HNA-2 null |
| HNA-3 (1) | rs147820753 | C > T | rs147820753 CC, rs2288904 GG: HNA-3a<br>rs147820753 CC, rs2288904 AA: HNA-3b |
| HNA-3 (2) | rs2288904 | A > G, T | rs147820753 TT, rs2288904 GG: HNA-3a<br>rs147820753 CT, rs2288904 GG: HNA-3a<br>rs147820753 CT, rs2288904 GA: HNA-3ab<br>rs147820753 CC, rs2288904 GA: HNA-3ab |
| HNA-4 | rs1143679 | G > A | HNA-4a: GG, HNA-4b: AA, HNA-4ab: GA |
| HNA-5 | rs2230433 | G > C | HNA-5a: GG, HNA-5bw: CC, HNA-5abw: GC |

Note: an HNA-1 coded gene is located on a minus strand, and phenotypic SNP sequences are based on coding strand information.

On yet another hand, the present invention provides a kit for genotyping, and a primer combination includes the primer combination of one of Tables 1 to 6 above.

On yet another hand, the present invention provides a method for genotyping by mass spectrometry detection, mainly including the following steps:

(1) by using an amplification primer mix in the above primer combination (the primer combination in any of Tables 1 to 6, these primers are all added to an amplification tube one time, and multiplex amplification is conducted simultaneously), amplifying genes to be detected by multiplex PCR;

(2) purifying an amplification product obtained in Step (1) by an alkaline phosphatase;

(3) by using an extension primer mix in the above primer combination (the extension primer combination in any of Tables 1 to 6, these primers are all added to an amplification tube one time, and extension of products are conducted simultaneously), extending and amplifying a purified product in Step (2) by a single base; and (4) conducting sample application on a single-base extended product obtained in Step (3) onto a chip for mass spectrometry detection.

Further, during multiplex PCR reaction in Step (1), a final concentration of each primer in the amplification primer mix used is 0.1 to 1 μM.

Further, a multiplex PCR reaction system in Step (1) is as follows.

TABLE 8

Multiplex PCR amplification reaction system

| Components | Volume (μL) |
|---|---|
| Water, HPLC grade | 0.8 |
| 10 × PCR Buffer with 20 mM MgCl$_2$ | 0.5 |
| 25 mM MgCl$_2$ | 0.4 |
| 25 mMdNTP Mix (dNTP mix) | 0.1 |
| 0.5 to 5 uM Primer Mix (primer combination) | 1 |
| 5 U/μl PCR Enzyme (PCR polymerase) | 0.2 |
| 5 to 20 ng/μL DNA (DNA to be detected) | 2 |
| Total volume | 5 |

The DNA to be detected may be DNA extracted from a blood sample as a template for amplification, such as platelet DNA, glycoprotein DNA or neutrophil DNA, or a mix of these DNAs is used as a template for amplification.

Further, an annealing temperature of the multiplex PCR reaction in Step (1) is 65° C. to 53° C.

Further, cycle conditions of the multiplex PCR reaction in Step (1) are as follows: (97° C., 5 minutes, 15 cycles, decreasing by 0.8° C. each cycle): (97° C., 30 seconds, 65° C. (decreasing by 0.8° C. each cycle from a second cycle), 45 seconds, 15 cycles); 72° C., 2 minutes; (97° C., 30 seconds, 53° C., 45 seconds, 72° C., 2 minutes, 32 cycles); 72° C., 7 minutes; keeping a temperature of 4° C.

Further, the alkaline phosphatase in Step (2) is a shrimp alkaline phosphatase, and a premixed solution system for purification treatment with the alkaline phosphatase in Step (2) is shown in Table 9.

22

TABLE 9

SAP premixed solution system

| Components | Volume (μL) |
|---|---|
| Nanopure Water, Autoclaved (ultrapure water) | 1.53 |
| SAP Buffer | 0.17 |
| SAP Enzyme (1.7 U/ul) (shrimp alkaline phosphatase) | 0.30 |
| Total volume | 2 |

Further, a single-base extension premixed solution system in Step (3) is shown in Table 10.

TABLE 10

Single-base extension premixed solution system

| Components | Volume (μL) |
|---|---|
| Nanopure Water, Autoclaved (ultrapure water) | 0.619 |
| iPLEX Buffer (extension buffer) | 0.200 |
| iPLEX Termination Mix (extension termination mix) | 0.200 |
| Extend Primer Mix (extension primer combination) | 0.94 |
| iPLEX Enzyme (single-base extension reaction enzyme) | 0.041 |
| Total volume | 2 |

On yet another hand, the present invention provides use of the above primer combination for preparing a mass spectrometry chip for genotyping of any one or more of platelet antigens, neutrophil antigens and CD36.

On yet another hand, the present invention provides use of the above primer combination or the above kit for genotyping mass spectrometry detection of any one or more of platelet antigens, neutrophil antigens and CD36.

A mass spectrometry-based method and a kit for genotyping of platelet and neutrophil antigens and glycoproteins provided by the present invention have the following beneficial effects.

1. All 35 platelet-specific antigen polymorphic sites, 10 CD36 polymorphic sites and 8 neutrophil antigen polymorphic sites can be simultaneously detected in 2 reactions, and the most comprehensive typing detection for all platelet antigens, CD36 and neutrophil antigens one time is achieved; 2. high specificity and sensitivity, and fast and high throughput are achieved; 3. the present invention can be used in clinic, scientific research, platelet donor routine screening, etc.

DETAILED DESCRIPTION OF EMBODIMENTS

Figure 1:
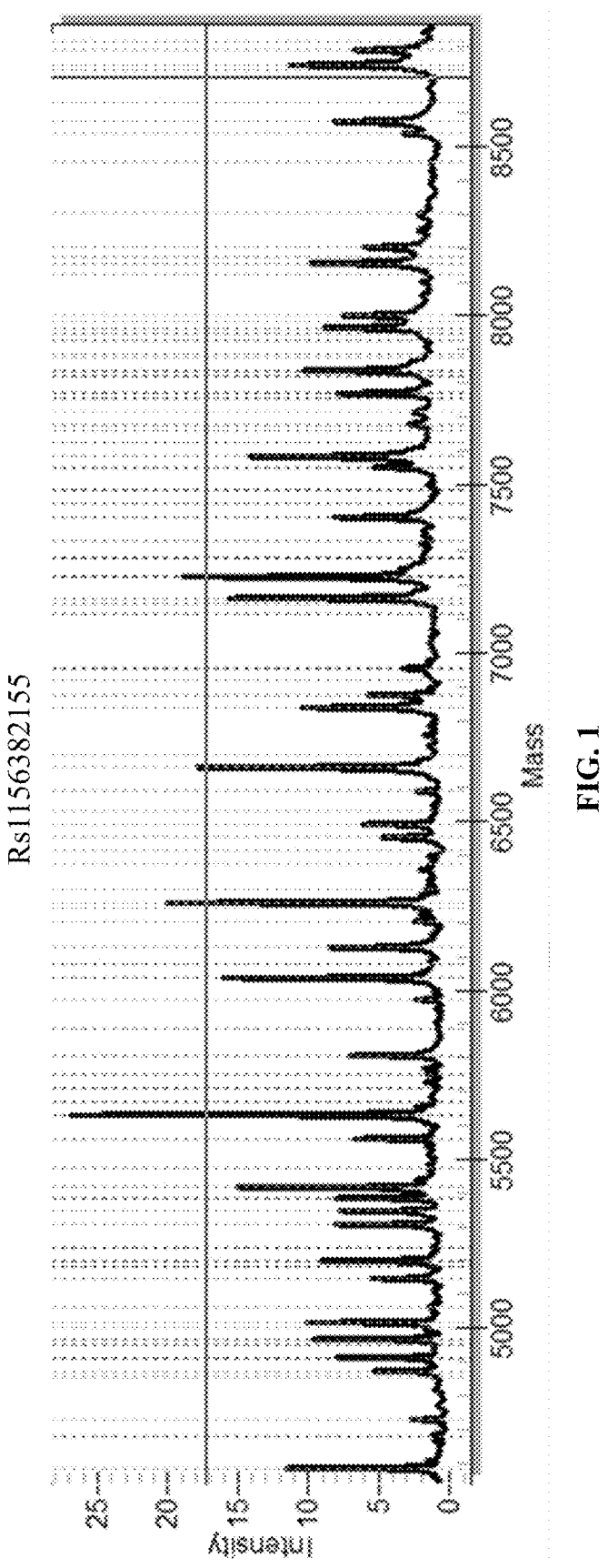
FIG. 1 is a representative detection mass spectrogram provided by Embodiment 1.

The present invention will be further described in detail below in combination with embodiments. It should be pointed out that the following embodiments are intended to facilitate the understanding of the present invention, but do not have any limiting effect on it. Reagents used in the embodiments are all known products, and are obtained by purchasing commercially available products.

Embodiment 1 Methods and Steps for Genotyping Detection of Platelet Antigens, Neutrophil Antigens and CD36

In this embodiment, 35 platelet-specific antigen polymorphic sites, 10 CD36 polymorphic sites and 8 neutrophil antigen polymorphic sites are simultaneously detected on 400 cases of blood gene DNAs, so as to conduct genotyping. Although this embodiment only provides that the 35 platelet-specific antigen polymorphic sites, the 10 CD36 polymorphic sites and the 8 neutrophil antigen polymorphic sites are simultaneously detected, it can be understood that primer groups for the 10 CD36 polymorphic sites can also be used for simultaneous detection of the 10 polymorphic sites of CD36; primer groups for any one or more of the 35 platelet-specific antigen polymorphic sites, the 10 CD36 polymorphic sites and the 8 neutrophil antigen polymorphic sites can also be used for genotyping detection of any one or more thereof.

The genotyping detection of this embodiment includes the following steps.

1. Sample Preparation:

Genes (DNAs) of 400 cases of blood samples are extracted, and concentrations thereof are normalized to 5 to 20 ng/μL for subsequent detection experiments.

2. Primer Design

Amplification primers and extension primers are designed to detect 35 polymorphic sites of HPA1-35, 8 polymorphic sites of HNA1-5 and 10 polymorphic sites related to a CD36 deletion phenotype in CD36 protein coding genes. Amplification is divided into 2 test tubes or PCR tubes (repeated 2 times). In each test tube, forward and reverse primers in Table 11 are added one time to detect each site one time, and primer sequences are shown in Table 12.

TABLE 11

| Designed primer groups | | | | |
| --- | --- | --- | --- | --- |
| Detected genes | SNP sites | Forward primers | Reverse primers | Extension primers |
| CD36 (1) | rs550565800 | SEQ ID NO: 1 | SEQ ID NO: 2 | SEQ ID NO: 3 |
| CD36 (2) | rs75326924 | SEQ ID NO: 4 | SEQ ID NO: 5 | SEQ ID NO: 6 |
| CD36 (3) | rs572295823 | SEQ ID NO: 7 | SEQ ID NO: 8 | SEQ ID NO: 9 |
| CD36 (4) | rs201355711 | SEQ ID NO: 10 | SEQ ID NO: 11 | SEQ ID NO: 12 |
| CD36 (5) | rs148910227 | SEQ ID NO: 13 | SEQ ID NO: 14 | SEQ ID NO: 15 |
| CD36 (6) | rs201765331 | SEQ ID NO: 16 | SEQ ID NO: 17 | SEQ ID NO: 18 |
| CD36 (7) | rs545489204 | SEQ ID NO: 19 | SEQ ID NO: 20 | SEQ ID NO: 21 |
| CD36 (8) | rs142186404 | SEQ ID NO: 22 | SEQ ID NO: 23 | SEQ ID NO: 24 |
| CD36 (9) | rs201759307 | SEQ ID NO: 25 | SEQ ID NO: 26 | SEQ ID NO: 27 |
| CD36 (10) | rs767892046 | SEQ ID NO: 28 | SEQ ID NO: 29 | SEQ ID NO: 30 |
| HPA-1 | rs5918 | SEQ ID NO: 31 | SEQ ID NO: 32 | SEQ ID NO: 33 |
| HPA-2 | rs6065 | SEQ ID NO: 34 | SEQ ID NO: 35 | SEQ ID NO: 36 |
| HPA-3 | rs5911 | SEQ ID NO: 37 | SEQ ID NO: 38 | SEQ ID NO: 39 |
| HPA-4 | rs5917 | SEQ ID NO: 40 | SEQ ID NO: 41 | SEQ ID NO: 42 |
| HPA-5 | rs1801106 | SEQ ID NO: 43 | SEQ ID NO: 44 | SEQ ID NO: 45 |
| HPA-6w | rs13306487 | SEQ ID NO: 46 | SEQ ID NO: 47 | SEQ ID NO: 48 |
| HPA-7w | rs121918448 | SEQ ID NO: 49 | SEQ ID NO: 50 | SEQ ID NO: 51 |
| HPA-8w | rs151219882 | SEQ ID NO: 52 | SEQ ID NO: 53 | SEQ ID NO: 54 |
| HPA-9w | rs74988902 | SEQ ID NO: 55 | SEQ ID NO: 56 | SEQ ID NO: 57 |
| HPA-10w | rs200358667 | SEQ ID NO: 58 | SEQ ID NO: 59 | SEQ ID NO: 60 |
| HPA-11w | rs377302275 | SEQ ID NO: 61 | SEQ ID NO: 62 | SEQ ID NO: 63 |
| HPA-12w | rs375285857 | SEQ ID NO: 64 | SEQ ID NO: 65 | SEQ ID NO: 66 |
| HPA-13w | rs79932422 | SEQ ID NO: 67 | SEQ ID NO: 68 | SEQ ID NO: 69 |
| HPA-14w | HPA-14w | SEQ ID NO: 70 | SEQ ID NO: 71 | SEQ ID NO: 72 |
| HPA-15 | rs10455097 | SEQ ID NO: 73 | SEQ ID NO: 74 | SEQ ID NO: 75 |
| HPA-16w | rs74708909 | SEQ ID NO: 76 | SEQ ID NO: 77 | SEQ ID NO: 78 |
| HPA-17w | rs770992614 | SEQ ID NO: 79 | SEQ ID NO: 80 | SEQ ID NO: 81 |
| HPA-18w | rs267606593 | SEQ ID NO: 82 | SEQ ID NO: 83 | SEQ ID NO: 84 |
| HPA-19w | rs80115510 | SEQ ID NO: 85 | SEQ ID NO: 86 | SEQ ID NO: 87 |
| HPA-20w | rs78299130 | SEQ ID NO: 88 | SEQ ID NO: 89 | SEQ ID NO: 90 |
| HPA-21w | rs70940817 | SEQ ID NO: 91 | SEQ ID NO: 92 | SEQ ID NO: 93 |
| HPA-22w | rs 142811900 | SEQ ID NO: 94 | SEQ ID NO: 95 | SEQ ID NO: 96 |

TABLE 11-continued

| Designed primer groups | | | | |
| --- | --- | --- | --- | --- |
| Detected genes | SNP sites | Forward primers | Reverse primers | Extension primers |
| HPA-23w | rs139166528 | SEQ ID NO: 97 | SEQ ID NO: 98 | SEQ ID NO: 99 |
| HPA-24w | rs281864910 | SEQ ID NO: 100 | SEQ ID NO: 101 | SEQ ID NO: 102 |
| HPA-25w | rs771035051 | SEQ ID NO: 103 | SEQ ID NO: 104 | SEQ ID NO: 105 |
| HPA-26w | rs1156382155 | SEQ ID NO: 106 | SEQ ID NO: 107 | SEQ ID NO: 108 |
| HPA-27w | rs 149468422 | SEQ ID NO: 109 | SEQ ID NO: 110 | SEQ ID NO: 111 |
| HPA-28w | rs368953599 | SEQ ID NO: 112 | SEQ ID NO: 113 | SEQ ID NO: 114 |
| HPA-29w | rs544276300 | SEQ ID NO: 115 | SEQ ID NO: 116 | SEQ ID NO: 117 |
| HPA-30w | rs377753373 | SEQ ID NO: 118 | SEQ ID NO: 119 | SEQ ID NO: 120 |
| HPA-31w | rs202229101 | SEQ ID NO: 121 | SEQ ID NO: 122 | SEQ ID NO: 123 |
| HPA-32w | rs879083862 | SEQ ID NO: 124 | SEQ ID NO: 125 | SEQ ID NO: 126 |
| HPA-33w | rs1555572829 | SEQ ID NO: 127 | SEQ ID NO: 128 | SEQ ID NO: 129 |
| HPA-34w | rs777748046 | SEQ ID NO: 130 | SEQ ID NO: 131 | SEQ ID NO: 132 |
| HPA-35w | rs779974422 | SEQ ID NO: 133 | SEQ ID NO: 134 | SEQ ID NO: 135 |
| HNA-1 (1) | rs448740 | SEQ ID NO: 136 | SEQ ID NO: 137 | SEQ ID NO: 138 |
| HNA-1 (2) | rs5030738 | SEQ ID NO: 139 | SEQ ID NO: 140 | SEQ ID NO: 141 |
| HNA-2 (1) | rs777225032 | SEQ ID NO: 142 | SEQ ID NO: 143 | SEQ ID NO: 144 |
| HNA-2 (2) | rs1230516223 | SEQ ID NO: 145 | SEQ ID NO: 146 | SEQ ID NO: 147 |
| HNA-3 (1) | rs147820753 | SEQ ID NO: 148 | SEQ ID NO: 149 | SEQ ID NO: 150 |
| HNA-3 (2) | rs2288904 | SEQ ID NO: 151 | SEQ ID NO: 152 | SEQ ID NO: 153 |
| HNA-4 | rs1l43679 | SEQ ID NO: 154 | SEQ ID NO: 155 | SEQ ID NO: 156 |
| HNA-5 | rs2230433 | SEQ ID NO: 157 | SEQ ID NO: 158 | SEQ ID NO: 159 |

3. Detection Steps

1) PCR Amplification

All amplification primer combinations shown in Table 12 are used to be added to each amplification test tube (including forward primers and reverse primers), and genes to be detected obtained in Step 1 are amplified by multiplex PCR to obtain target sequence amplification products of samples to be detected.

A PCR amplification reaction system is shown in Table 12.

TABLE 12

| Multiplex PCR amplification reaction system | |
| --- | --- |
| Components | Volume (μL) |
| Water, HPLC grade | 0.8 |
| 10 x PCR Buffer with 20 mM MgCl₂ | 0.5 |
| 25 mM MgCl₂ | 0.4 |
| 25 mMdNTP Mix (dNTP mix) | 0.1 |
| 0.5 to 5 uM Primer Mix (primer combination) | 1 |

TABLE 12-continued

| Multiplex PCR amplification reaction system | |
| --- | --- |
| Components | Volume (μL) |
| 5 U/μl PCR Enzyme (PCR polymerase) | 0.2 |
| 5 to 20 ng/μL DNA (DNA to be detected) | 2 |
| Total volume | 5 |

Cycle conditions of PCR amplification reaction are as follows: (97° C., 5 minutes, 15 cycles, decreasing by 0.8° C. each cycle): (97° C., 30 seconds, 65° C. (decreasing by 0.8° C. each cycle from a second cycle), 45 seconds, 15 cycles); 72° C., 2 minutes; (97° C., 30 seconds, 53° C., 45 seconds, 72° C., 2 minutes, 32 cycles); 72° C., 7 minutes; keeping a temperature of 4° C.

2) Treatment with a Shrimp Alkaline Phosphatase (SAP)

Remaining dNTPs are treated by the shrimp alkaline phosphatase (SAP) to prevent interference with subsequent base extension. An SAP premixed solution system is shown in Table 13.

TABLE 13

| SAP premixed solution system | |
| --- | --- |
| Components | Volume (μL) |
| Nanopure Water, Autoclaved (ultrapure water) | 1.53 |
| SAP Buffer | 0.17 |
| SAP Enzyme (1.7 U/ul) (shrimp alkaline phosphatase) | 0.30 |
| Total volume | 2 |

In Step 1), 2 μl of an SAP premixed solution is added to each reaction well of the 2 test tubes after PCR amplification, a total volume after the mixed solution is added is 7 and then SAP reaction is conducted in an amplification instrument. Reaction programs are as follows: 37° C., 40 minutes; 85° C., 5 minutes; keeping a temperature of 4° C.

3) Base Extension

All extension primer combinations shown in Table 12 are used to be added to test tubes respectively, and purified products in Step 2) are amplified by single-base extension. Through this amplification, a sequence-specific single base is extended at a 3' end of an extension probe as a molecular weight marker. A single-base extension premixed solution system is shown in Table 14.

TABLE 14

| Single-base extension premixed solution system | |
| --- | --- |
| Components | Volume (μL) |
| Nanopure Water, Autoclaved (ultrapure water) | 0.619 |
| iPLEX Buffer (extension buffer) | 0.200 |
| iPLEX Termination Mix (extension termination mix) | 0.200 |
| Extend Primer Mix (extension primer combination) | 0.94 |
| iPLEX Enzyme (single-base extension reaction enzyme) | 0.041 |
| Total volume | 2 |

In Step 2), 2 μl of an extension premixed solution is added to each test tube after treatment with the shrimp alkaline phosphatase (SAP), a total volume after the mixed solution is added is 9 and then extension reaction is conducted in an amplification instrument.

Single-base extension reaction programs are as follows: 95° C., 30 seconds; (95° C., 5 seconds; (52° C., 5 seconds, 80° C., 5 seconds; 5 cycles) 40 cycles); 72° C., 3 minutes; keeping a temperature of 4° C.

4) Desalination with Resin

41 μl of HPLC water is added to each tube, resin is used for sample desalination, and extension reaction products are purified.

5) Mass Spectrometry Detection

After 2 test tubes of final desalination and purification, samples are subjected to sample application onto a chip (Manufacturer: Agena Bioscience, Model: SpectroCHIP CPM96). Molecular weight detection is performed by a mass spectrometer to determine the species of specific bases and the type of samples to be detected.

6) Result Analysis

Mass spectrometry detection is performed on the 400 cases of samples, and all sites have good results in all the samples (mass spectrometry software is rated A (Conservative) or B (Mordarate)). An obtained representative detection mass spectrogram is shown in FIG. 1. Among them, all sites of 34 randomly selected cases are sequenced. Results of mass spectrometry-based genotyping detection of platelet and neutrophil antigens and CD36 glycoproteins are completely consistent with sequencing results (see Table 15 for statistics of sequencing verification results).

Sensitivity=true positive results/(true positive results+false negative results)*100%=100%.

Specificity=the number of true negatives/(the number of true negatives+the number of false positives) *100%=100%.

TABLE 15

| Table for statistics of sequencing verification results | | | |
| --- | --- | --- | --- |
| Genes | Genotyping results | | |
| HPA-1 | HPA-1aa | HPA-1ab | HPA-1bb |
| | 32 | 2 | 0 |
| HPA-2 | HPA-2aa | HPA-2ab | HPA-2bb |
| | 33 | 1 | 0 |
| HPA-3 | HPA-3aa | HPA-3ab | HPA-3bb |
| | 13 | 16 | 5 |
| HPA-4 | HPA-4aa | HPA-4ab | HPA-4bb |
| | 33 | 1 | 0 |
| HPA-5 | HPA-5aa | HPA-5ab | HPA-5bb |
| | 32 | 2 | 0 |
| HPA-6w | HPA-6aa | HPA-6ab | HPA-6bb |
| | 29 | 4 | 0 |
| HPA-7w | HPA-7aa | HPA-7ab | HPA-7bb |
| | 34 | 0 | 0 |
| HPA-8w | HPA-8aa | HPA-8ab | HPA-8bb |
| | 34 | 0 | 0 |
| HPA-9w | HPA-9aa | HPA-9ab | HPA-9bb |
| | 34 | 0 | 0 |
| HPA-10w | HPA-10aa | HPA-10ab | HPA-10bb |
| | 34 | 0 | 0 |
| HPA-11w | HPA-11aa | HPA-11ab | HPA-11bb |
| | 34 | 0 | 0 |
| HPA-12w | HPA-12aa | HPA-12ab | HPA-12bb |
| | 34 | 0 | 0 |
| HPA-13w | HPA-13aa | HPA-13ab | HPA-13bb |
| | 34 | 0 | 0 |
| HPA-14w | HPA-14aa | HPA-14ab | HPA-14bb |
| | 34 | 0 | 0 |
| HPA-15 | HPA-15aa | HPA-15ab | HPA-15bb |
| | 8 | 20 | 6 |
| HPA-16w | HPA-16aa | HPA-16ab | HPA-16bb |
| | 34 | 0 | 0 |
| HPA-17w | HPA-17aa | HPA-17ab | HPA-17bb |
| | 34 | 0 | 0 |
| HPA-18w | HPA-18aa | HPA-18ab | HPA-18bb |
| | 34 | 0 | 0 |
| HPA-19w | HPA-19aa | HPA-19ab | HPA-19bb |
| | 34 | 0 | 0 |
| HPA-20w | HPA-20aa | HPA-20ab | HPA-20bb |
| | 34 | 0 | 0 |
| HPA-21w | HPA-21aa | HPA-21ab | HPA-21bb |
| | 31 | 3 | 0 |
| HPA-22w | HPA-22aa | HPA-22ab | HPA-22bb |
| | 34 | 0 | 0 |
| HPA-23w | HPA-23aa | HPA-23ab | HPA-23bb |
| | 34 | 0 | 0 |
| HPA-24w | HPA-24aa | HPA-24ab | HPA-24bb |
| | 34 | 0 | 0 |
| HPA-25w | HPA-25aa | HPA-25ab | HPA-25bb |
| | 34 | 0 | 0 |
| HPA-26w | HPA-26aa | HPA-26ab | HPA-26bb |
| | 34 | 0 | 0 |
| HPA-27w | HPA-27aa | HPA-27ab | HPA-27bb |
| | 34 | 0 | 0 |
| HPA-28w | HPA-28aa | HPA-28ab | HPA-28bb |
| | 34 | 0 | 0 |
| HPA-29w | HPA-29aa | HPA-29ab | HPA-29bb |
| | 34 | 0 | 0 |
| HPA-30w | HPA-30aa | HPA-30ab | HPA-30bb |
| | 34 | 0 | 0 |

TABLE 15-continued

| Table for statistics of sequencing verification results | | | |
|---|---|---|---|
| Genes | Genotyping results | | |
| HPA-31w | HPA-31aa | HPA-31ab | HPA-31bb |
| | 34 | 0 | 0 |
| HPA-32w | HPA-32aa | HPA-32ab | HPA-32bb |
| | 34 | 0 | 0 |
| HPA-33w | HPA-33aa | HPA-33ab | HPA-33bb |
| | 34 | 0 | 0 |

TABLE 15-continued

| Table for statistics of sequencing verification results | | | | | |
|---|---|---|---|---|---|
| Genes | Genotyping results | | | | |
| HPA-34w | HPA-34aa | HPA-34ab | HPA-34bb | | |
| | 34 | 0 | 0 | | |
| HPA-35w | HPA-35aa | HPA-35ab | HPA-35bb | | |
| | 34 | 0 | 0 | | |
| HNA-1 | HNA-1a | HNA-1ab | HNA-1bc | HNA-1abc | HNA-1b |
| | 7 | 23 | 0 | 0 | 6 |
| HNA-2 | HNA-2 | HNA-2 null | | | |
| | 34 | 0 | | | |
| HNA-3 | HNA-3a | HNA-3ab | HNA-3b | | |
| | 12 | 17 | 5 | | |
| HNA-4 | HNA-4a | HNA-4ab | HNA-4b | | |
| | 34 | 0 | 0 | | |
| HNA-5 | HNA-5a | HNA-5ab | HNA-5b | | |
| | 26 | 7 | 1 | | |
| CD36 | CD36+ | CD36het | CD36− | | |
| | 28 | 6 | 0 | | |

Embodiment 2 Exploration of Mass Spectrometry PCR Conditions for Platelet-Specific Antigen HPA12w HPA-12w is located on a GP1Bbeta gene (NM_000407), and is not on the same gene as other HPA systems. Its SNP site is located at rs375285857, and on a fragment of about 1,000 bp before and after 500 bp and is rich in GC (>75%). In a process of designing a mass spectrometer chip for HPA-1-35, existing primer sequences do not work well for first-step amplification of HPA-12w. This embodiment is optimized by the following steps: (1) available primers for monoplex PCR are screened; (2) PCR conditions are changed (a Touchdown annealing temperature is used); (3)

primer concentrations in multiplex PCR reaction are explored and optimized, HPA-12w is successfully introduced into a platelet group panel (gene combination), and conversion efficiency thereof is greater than 70%.

(1) Screening of Available Primers

In this embodiment, three pairs of primers shown in Table 16 are used, of which one pair cannot be amplified in monoplex PCR reaction (the primers are subjected to PCR reaction singly), and the other two pairs have products in monoplex PCR reaction of some samples, but they cannot be amplified in multiplex PCR reaction.

TABLE 16

Figure 2:
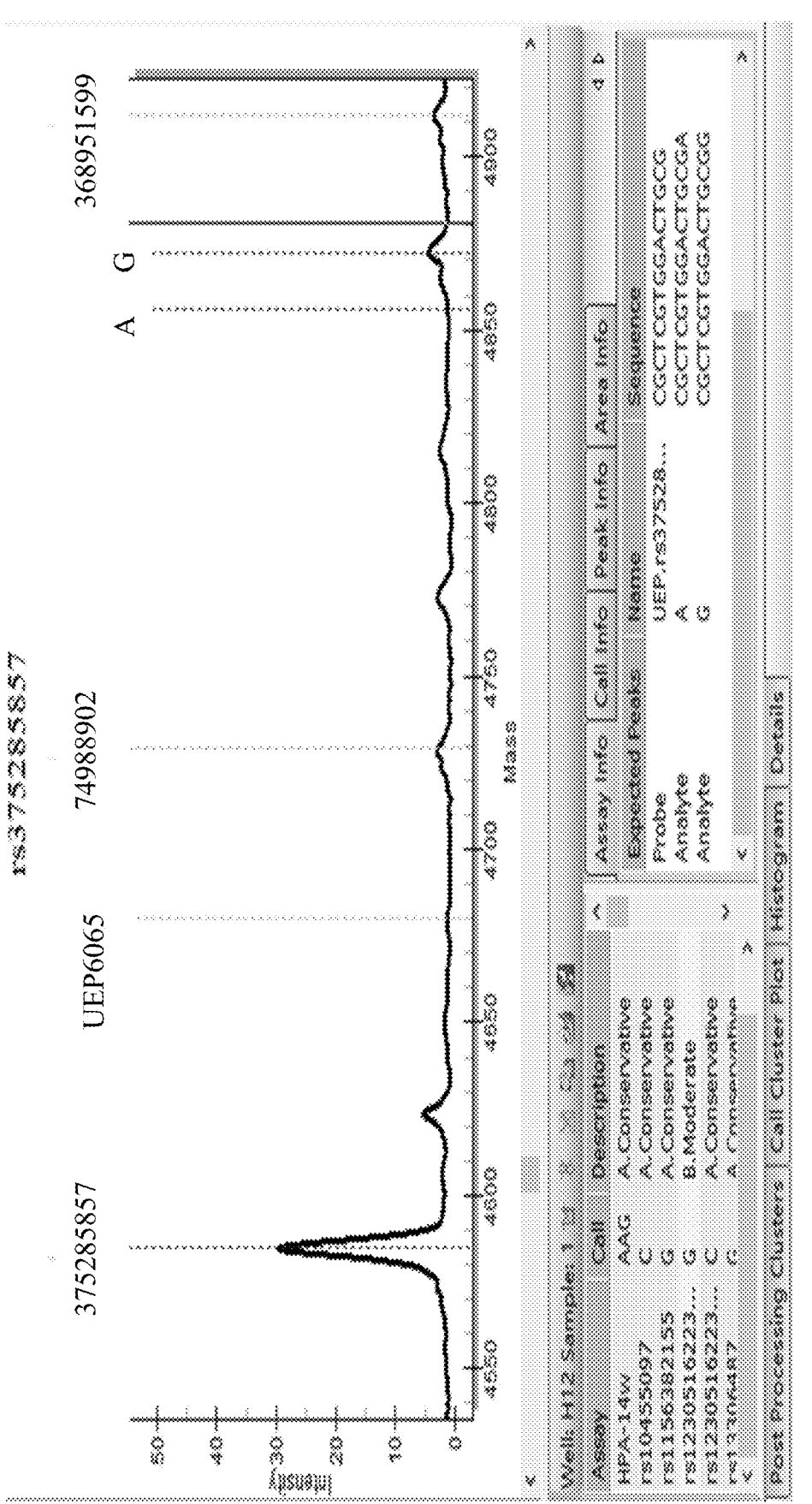
FIG. 2 is a detection mass spectrogram of amplification and detection of HPA12w by a second group of primers provided by Embodiment 2.
Figure 3:
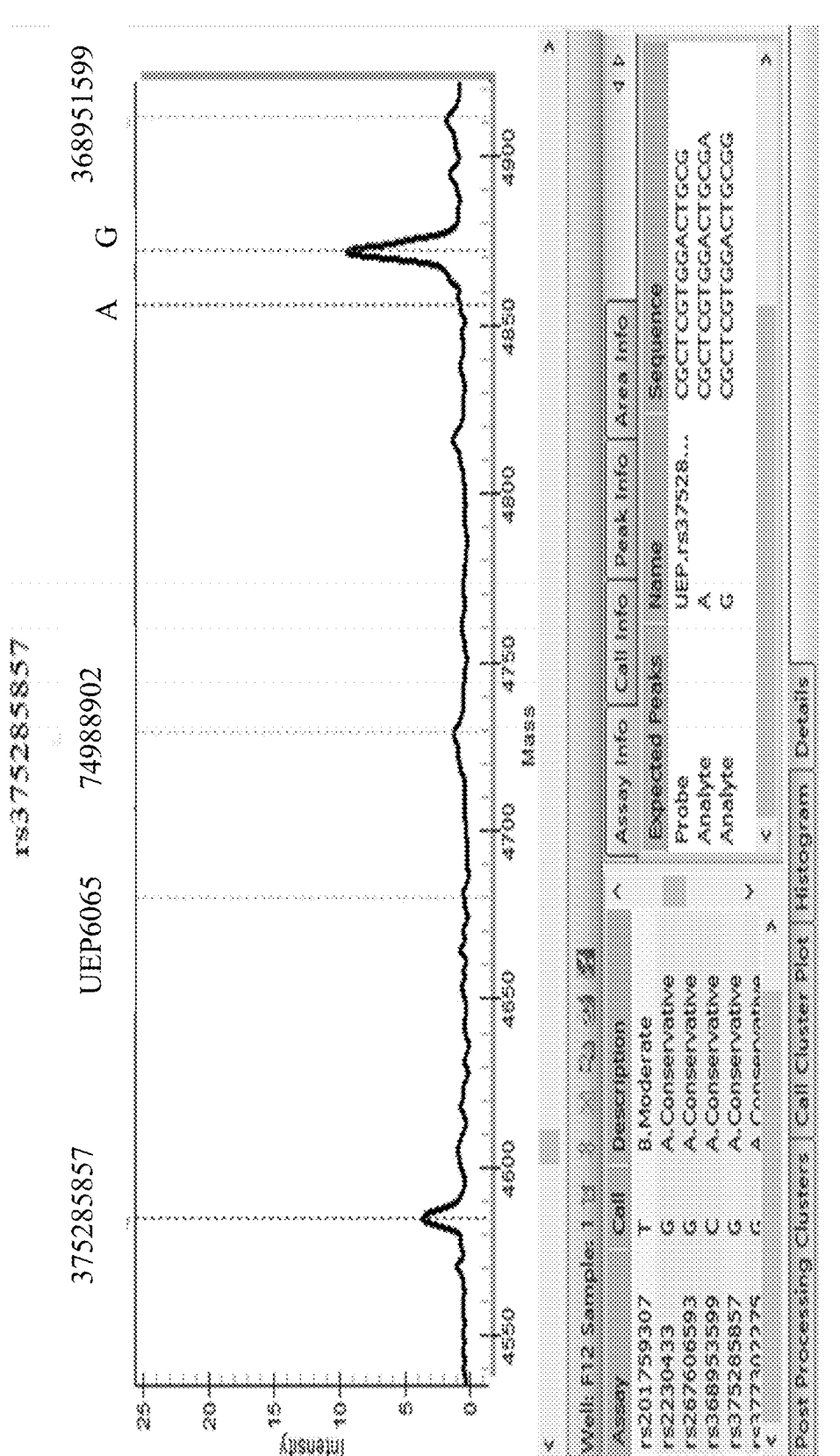
FIG. 3 is a detection mass spectrogram of amplification and detection of HPA12w by a third group of primers provided by Embodiment 2.

| List for screening of available primers for monoplex PCR | | | |
|---|---|---|---|
| Serial number | Forward primers | Reverse primers | Amplification results |
| 1 | ACGTTGGATGAGCTTAC TGCTCCTGCTG (SEQ ID NO: 160) | ACGTTGGATGTTGTGTCG ACAGGGAAGGC (SEQ ID NO: 161) | They cannot be amplified in monoplex PCR reaction (results shown) |
| 2 | ACGTTGGATGAGCTTAC TGCTCCTGCTGCT (SEQ ID NO: 162) | ACGTTGGATGGTTGTGTC GACAGGGAAGG (SEQ ID NO: 163) | There are products in monoplex reaction, but they cannot be amplified in multiplex reaction (FIG. 2) |
| 3 | ACGTTGGATGAGCTTAC TGCTCCTGCTGCT (SEQ ID NO: 64) | ACGTTGGATGTTGTGTCG ACAGGGAAGGC (SEQ ID NO: 65) | They can be successfully amplified and introduced into the platelet group panel (FIG. 3) |

Note:
primers involved in multiplex reaction here include primer pairs for 35 genetic sites on platelet-specific antigens. For example, when primers for other sites in Table 2 are combined, compared with the above three pairs of primers, the primers with serial number 3 can participate in multiplex amplification, and it can be successful.

It can be seen from Table 16 that the use of different amplification primers has a significant impact on the amplification effect of HPA12w during multiplex PCR reaction, so it is preferred to use the third group of amplification primers, so that HPA12w can be successfully introduced into a platelet group amplification system. Primer design is particularly important when multiplex amplification is used.

(2) Change of PCR Conditions (Using a Touchdown Annealing Temperature)

In this embodiment, three annealing temperatures shown in Table 17 are respectively used for multiplex PCR (35-plex amplification), to examine the influence of different annealing temperatures on detection results of HPA12w.

TABLE 17

| Influence of different annealing temperatures | | |
|---|---|---|
| Serial number | Annealing temperature (° C.) | Amplification results |
| 1 | 72-64 | Low conversion efficiency (20% to 51%) |
| 2 | 70-62 | General conversion efficiency (28% to 65%) |
| 3 | 68-60 | Highest conversion efficiency (70% to 95%) |

It can be seen from Table 17 that different annealing temperatures have a great impact on the conversion efficiency during multiplex PCR (35-plex amplification) reaction by using the above primer groups, and when the annealing temperature is too high, the conversion efficiency will be significantly reduced, therefore, a preferred annealing temperature is 68° C. to 60° C. in a process of designing a mass spectrometer chip for HPA1-35.

(3) Exploring and Optimizing of Amplification Primer Concentrations of an rs375285857 Site in Multiplex PCR Reaction When the multiplex PCR reaction (35-plex amplification) is performed according to the method shown in Embodiment 1, primer concentrations shown in Table 19 are respectively used for multiplex PCR amplification results. The primer concentrations mentioned here refer to final combinations of all primer combinations, in which, a final concentration of each primer is also 0.1 to 1 μM, as shown in Table 18.

TABLE 18

| Serial number | Primer concentration (μM) | Amplification results |
|---|---|---|
| | | Influence of different primer concentrations |
| 1 | 0.1 | General conversion efficiency (68% to 85%) |
| 2 | 0.2-0.3 | High conversion efficiency without affecting other sites (72% to 98%) |
| 3 | 0.3-0.5 | High conversion efficiency (75% to 97%) but affecting other sites, making HPA-5 or HPA-15 undetectable in some samples |
| 4 | 0.5-0.7 | High conversion efficiency (82% to 98%) but affecting other sites, making HPA-5 or HPA-15 undetectable in some samples |

It can be seen from Table 18 that different primer concentrations also have a significant impact on the multiplex PCR amplification reaction, when the primer concentration increases, although the conversion efficiency will also be improved, it will cause mutual influence between detection of different sites, resulting in that some sites cannot be detected, so a preferred primer concentration is 0.1 to 0.3 μM.

Embodiment 3 Exploration of Mass Spectrometry PCR Conditions for Neutrophil Antigen HNA-1

In a mass spectrometry kit, HNA-1 genotyping is determined by two SNP sites, namely rs5030738 and rs448740. Among them, rs448740 is located on an FCGR3B gene, and has a homologous gene FCGR3A, and a sequence thereof has a very high homology (~98%) with a sequence around rs448740.

(homologous sequences can be amplified), resulting in an error in a final typing result of mass spectrometry. In order to specifically amplify a fragment containing the rs448740 site and enable the fragment to be used for subsequent mass spectrometry steps, appropriate PCR primers need to be selected.

This embodiment adopts the following ways: (1) multiple random samples are selected, longer fragments containing rs448740 are amplified and sequencing is conducted to obtain accurate bases of the rs448740 site; (2) multiple PCR primers are designed, the above samples are used for test, and primers that can specifically amplify bands are selected; (3) the primers obtained in (2) are tested, primers with higher conversion efficiency after subsequent mass spectrometry steps are selected, and their concentrations in multiplex mass spectrometry are optimized. The selected primers can specifically amplify the fragment where rs448740 is located. Mass spectrometry typing results are completely consistent with sequencing typing results, and the conversion efficiency is greater than 70%.

(1) Screening of Available Primers

Primers selected in this embodiment are shown in Table 19. Different primers are respectively used for multiple PCR reaction (8 plexes), to examine an amplification effect of the rs448740 site.

TABLE 19

Figure 4:
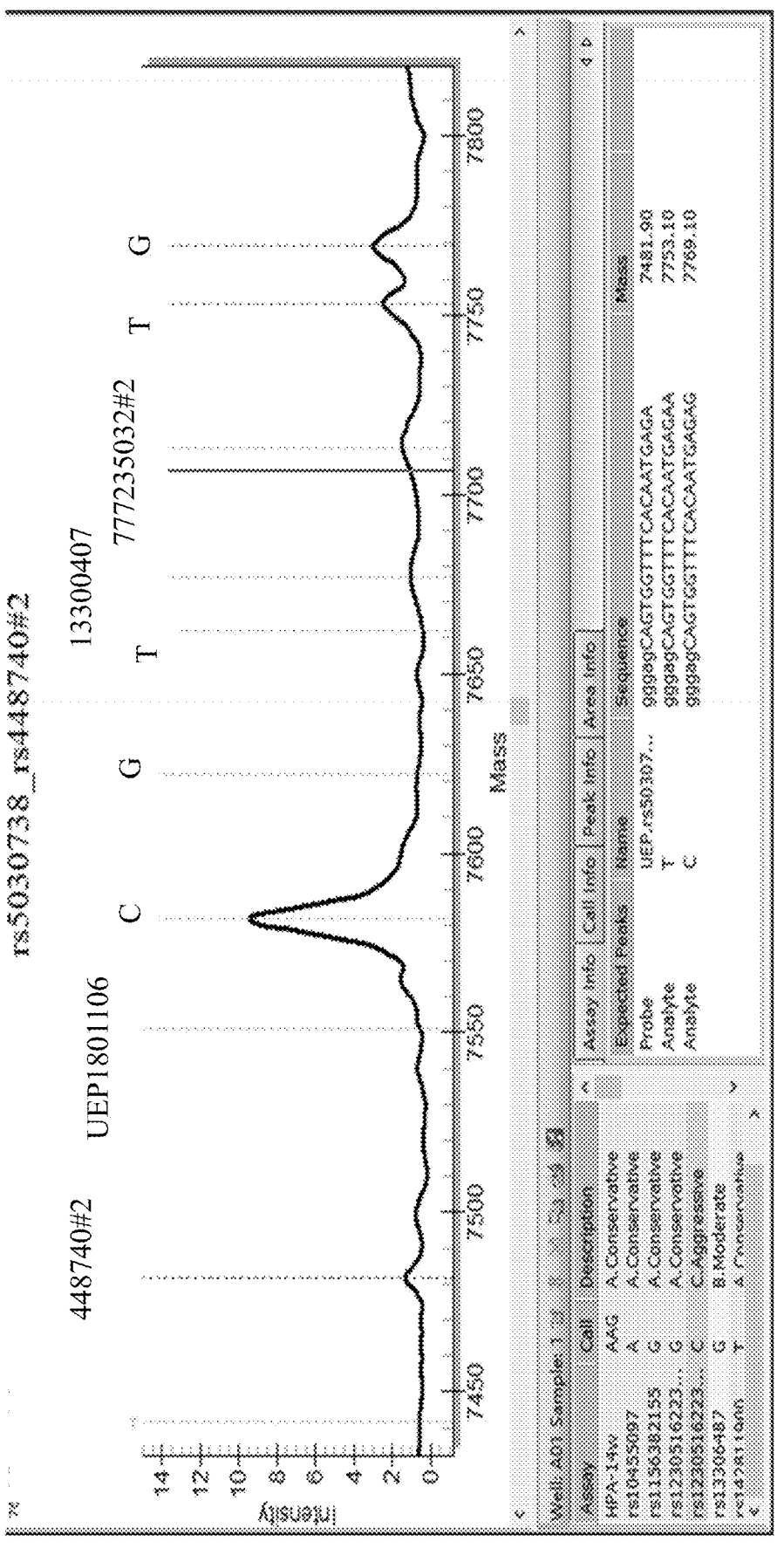
FIG. 4 is a detection mass spectrogram of amplification and detection of an rs448740 site by a third group of primers provided by Embodiment 3.
Figure 5:
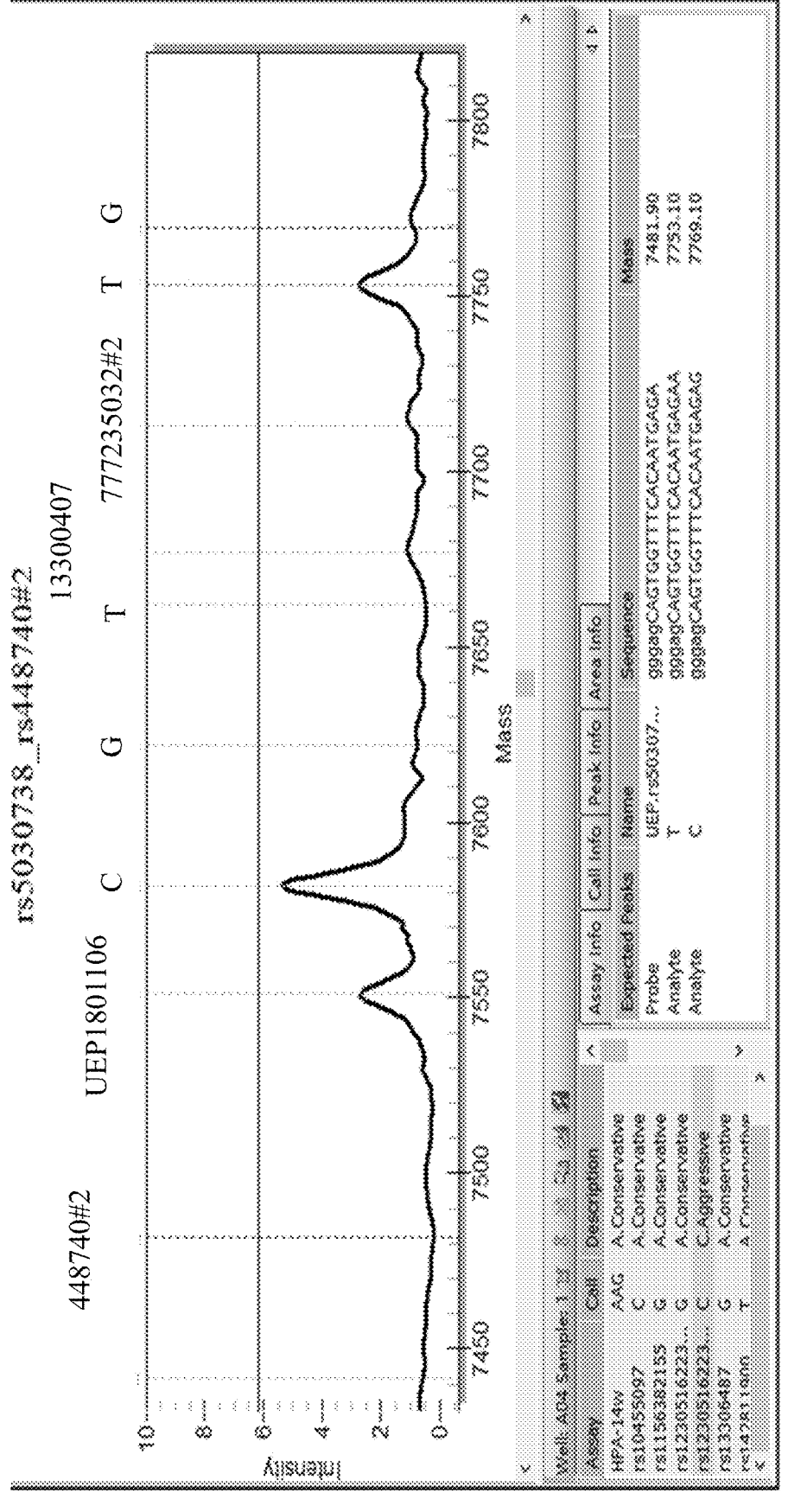
FIG. 5 is a detection mass spectrogram of amplification and detection of the rs448740 site by a fourth group of primers provided by Embodiment 3.
Figure 6:
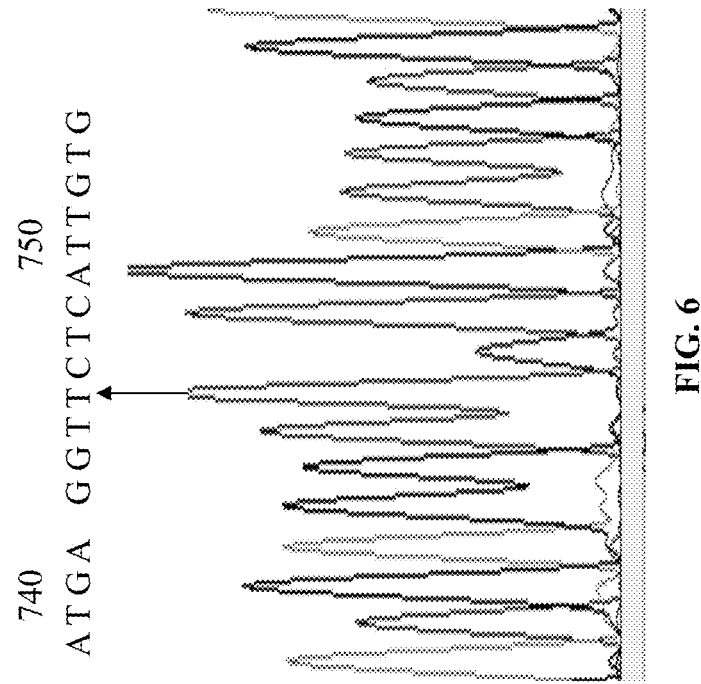
FIG. 6 shows sequencing results of amplification of samples by the third and fourth groups of primers provided by Embodiment 3.

| Serial number | Forward primers | Reverse primers | Amplification results |
|---|---|---|---|
| | | List for screened primers | |
| 1 | ACGTTGGATGCCTGTACTC TCCACTGTCGTT (SEQ ID NO: 164) | ACGTTGGATGCtTGGGAATG GCAGTGTAGA (SEQ ID NO: 165) | They cannot be amplified |
| 2 | ACGTTGGATGCCTGTACTC TCCACTGTCGTT (SEQ ID NO: 166) | ACGTTGGATGAAGCACGCTG TACCATTGAG (SEQ ID NO: 167) | They cannot be amplified or they are non-specifically amplified. |
| 3 | ACGTTGGATGCCTGTACTC TCCACTGTCGTT (SEQ ID NO: 168) | ACGTTGGATGCTCAATGGTA CAGCGTGCTT (SEQ ID NO: 169) | They are non-specifically amplified. (FIG. 4) |
| 4 | ACGTTGGATGTTGTCTGGC ACCTGTACTCT (SEQ ID NO: 118) | ACGTTGGATGCCCCTACTCA ATATTTGATTTAC (SEQ ID NO: 119) | The fragment where rs448740 is located is specifically amplified (FIG. 5) | rs448740. Therefore, rs448740 site amplification primers (V1) in existing mass spectrometry panel are non-specific It can be seen from Table 19 that the use of different amplification primers has a significant impact on the amplification effect of the rs448740 site during multiplex PCR reaction (8 plexes). When a first group of primers is used, the rs448740 site (8 plexes) cannot be amplified during genotyping detection of 8 sites of neutrophil antigens. When a second group of primers is used, sometimes they cannot be amplified, and sometimes they are non-specifically amplified, that is, a homologous gene FCGR3A is amplified simultaneously. When a third group of primers is used, there is also a problem of non-specific amplification. Only when a fourth group of primers is used, specific amplification can be successfully achieved. Therefore, it is preferable to use the fourth group of amplification primers, so that the rs448740 site can be successfully introduced into the neutrophil panel. FIG. 6 shows a sequencing map of tested samples in FIGS. 4 and 5 at the rs448740 site, and sequenced bases of this site are shown in a box. Sequencing results prove that a result in FIG. 5 amplified under conditions of the fourth group of primers is specific amplification.

(2) Exploring and Optimizing of Amplification Primer Concentrations of the rs448740 Site in Multiplex PCR Reaction When the multiplex PCR reaction is performed according to the method shown in Embodiment 1, primer concentrations shown in Table 19 are respectively used for multiplex PCR amplification results, as shown in Table 20.

TABLE 20

Influence of different primer concentrations

| Serial number | Primer concentration (µM) | Amplification results |
|---|---|---|
| 1 | 0.2 | General conversion efficiency (70% to 85%) |
| 2 | 0.4 | High conversion efficiency (72% to 96%) without affecting other sites |
| 3 | 0.6 | High conversion efficiency (78% to 96%) but affecting other sites, making HNA-2 (rs777225032), HPA-5 and HPA-12 undetectable in some samples |

It can be seen from Table 20 that different primer concentrations also have a significant impact on the multiplex PCR amplification reaction, when the primer concentration increases, although the conversion efficiency will also be improved, it will cause mutual influence between detection of different sites, resulting in that HNA-2 (rs777225032), HPA-5 and HPA-12 cannot be detected in some samples, so a preferred primer concentration is 0.2 to 0.4 µM.

Embodiment 4 Overall Condition Optimization

In this embodiment, the primers and primer concentrations obtained by exploration in Embodiment 3 are used for experiments, and it is found that there are 3 sites, namely HPA-5 (rs1801106), HPA-15 (rs10455097), and CD36 (1)

(rs550565800) with reduced efficiency or even no peaks. In order to stabilize peak appearance at all sites of the entire panel, no call is eliminated. This embodiment adopts the following ways: (1) two new PCR primer pairs (new1 and new2) are designed for the three sites respectively, and tested to select appropriate primer combinations; (2) PCR conditions are changed according to the characteristics of annealing temperatures of primers to select optimal amplification conditions; (3) a large number of samples are verified.

(1) Screening of Available Primers for Monoplex PCR

In this embodiment, 9 pairs of primers shown in Table 15 are used for three combinations (shown in Table 22), to examine an amplification effect on an overall site.

TABLE 21 selected primer sequences (5'-3')

| Sites | | Primer old | Primer new 1 | Primer new2 |
|---|---|---|---|---|
| rs1801106 | Forward | ACGTTGGATGGG AAGAGTCTACCT GTTTAC (SEQ ID NO: 170) | ACGTTGGATGAGACG TGCTCTTGGTAGGTG (SEQ ID NO: 43) | ACGTTGGATGGAAGG AAGAGTCTACCTGTTT AC (SEQ ID NO: 171) |
| | Reverse | ACGTTGGATGGTA AACCATACTATCT GTGC (SEQ ID NO: 172) | ACGTTGGATGCCAAA TGCAAGTTAAATTAC CAGT (SEQ ID NO: 44) | ACGTTGGATGGAAATG TAAACCATACTATCTGT GC (SEQ ID NO: 173) |

TABLE 21-continued

| selected primer sequences (5'-3') | | | |
| --- | --- | --- | --- |
| Sites | Primer old | Primer new 1 | Primer new2 |
| rs10455097 Forward | ACGTTGGATGCA AAATGTATCAGTT CTTGG (SEQ ID NO: 174) | ACGTTGGATGTCAGT TCTTGGTTTTGTGATG TT (SEQ ID NO: 73) | ACGTTGGATGTTATTTC AAAATGTATCAGTTCT TGG (SEQ ID NO: 175) |
| Reverse | ACGTTGGATGAG CCACCCAAGAAG TGATAG (SEQ ID NO: 176) | ACGTTGGATGCACAA AACCAGTAGCCACCC (SEQ ID NO: 74) | ACGTTGGATGAGCCAC CCTGATAG (SEQ ID NO: 177) |
| rs550565800 Forward | ACGTTGGATGCA GCTGCAAATACA AACCTC (SEQ ID NO: 178) | ACGTTGGATGGGAAC AAAATCAAATTAGCA ACAGC (SEQ ID NO: 1) | ACGTTGGATGAATTAG CAACAGCAACTAATTT ATG (SEQ ID NO: 179) |
| Reverse | ACGTTGGATGGC AACAGCAACTAA TTTATG (SEQ ID NO: 180) | ACGTTGGATGTTTTAA TGACTAACAGCTGCA AA (SEQ ID NO: 2) | ACGTTGGATGACAGCT GCAAATACAAACCTC (SEQ ID NO: 181) |

TABLE 22

Figure 7:
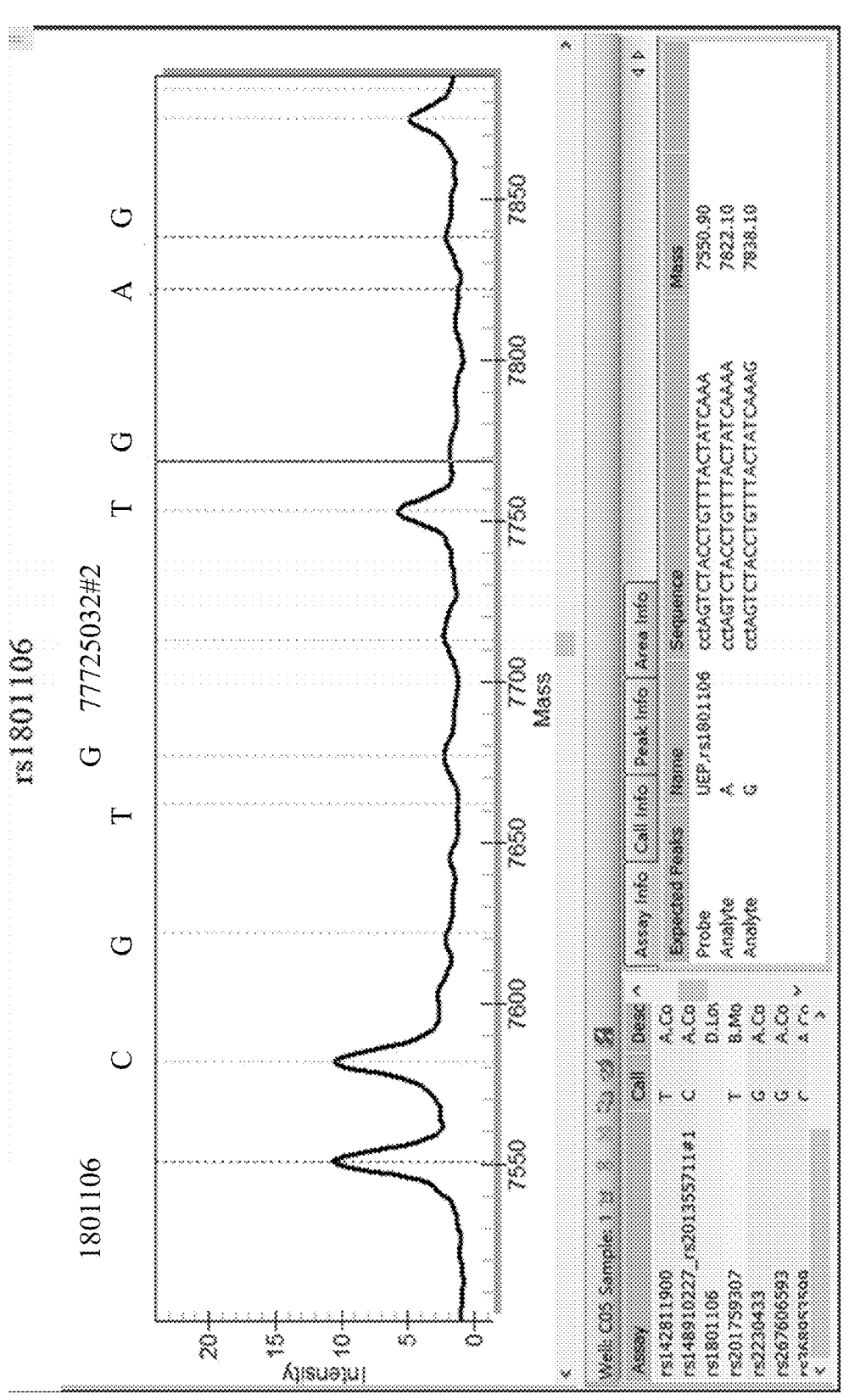
FIG. 7 is a detection mass spectrogram of amplification and detection of an HPA-5 (rs1801106) site by old primers provided by Embodiment 4.
Figure 8:
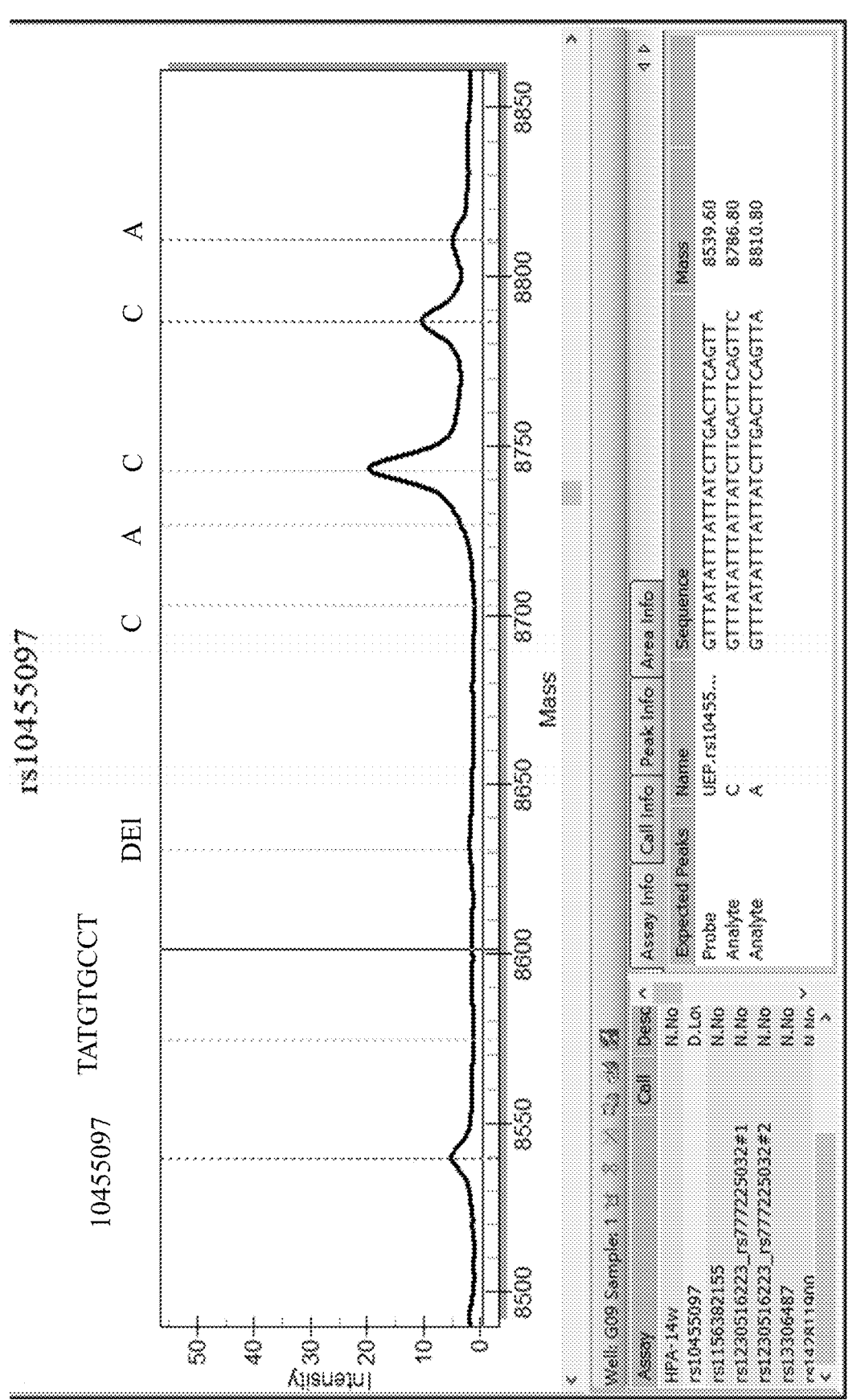
FIG. 8 is a detection mass spectrogram of amplification and detection of an HPA-15 (rs10455097) site by old primers provided by Embodiment 4.
Figure 9:
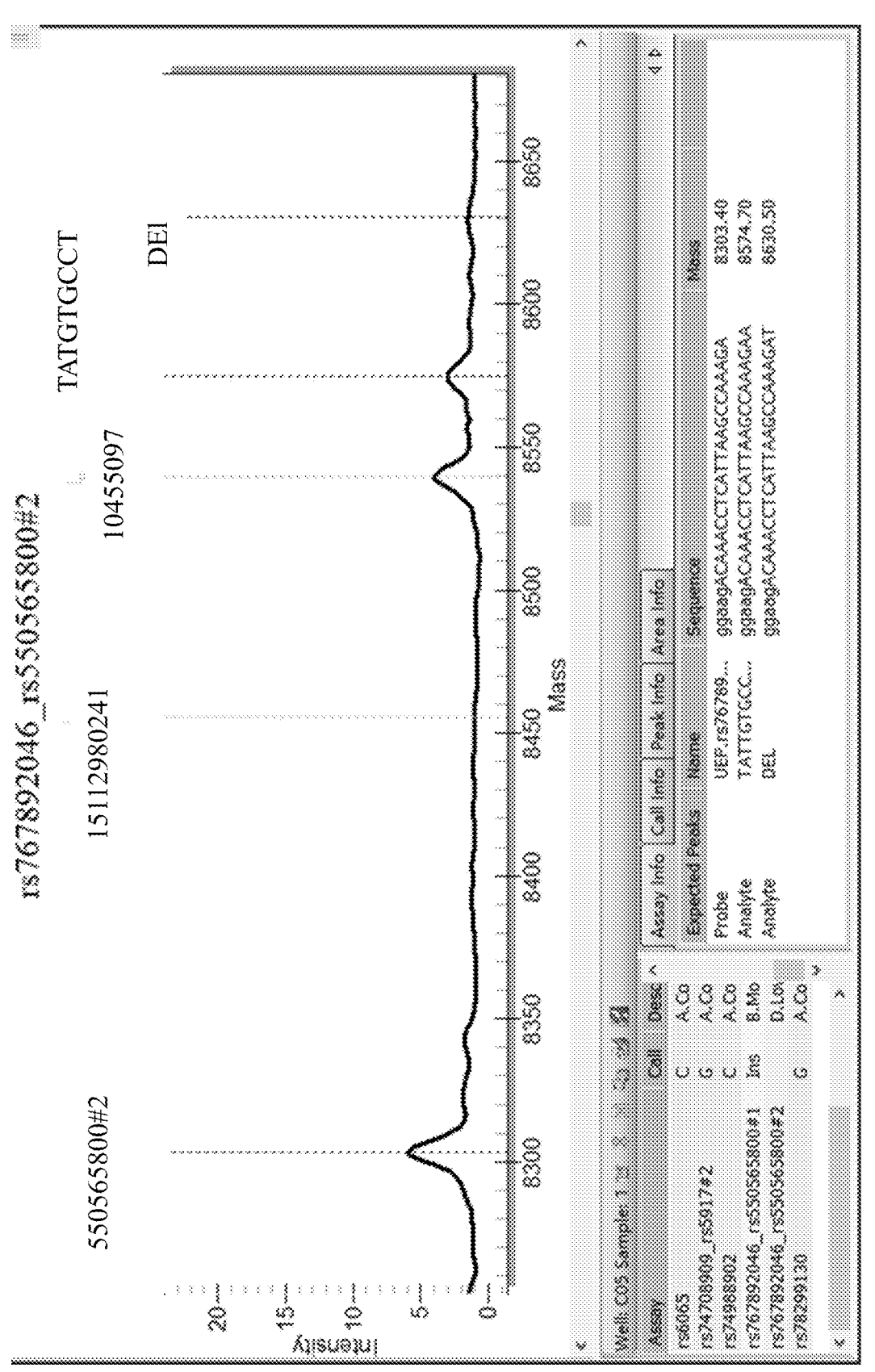
FIG. 9 is a detection mass spectrogram of amplification and detection of a CD36(1) (rs550565800) site by old primers provided by Embodiment 4.
Figure 10:
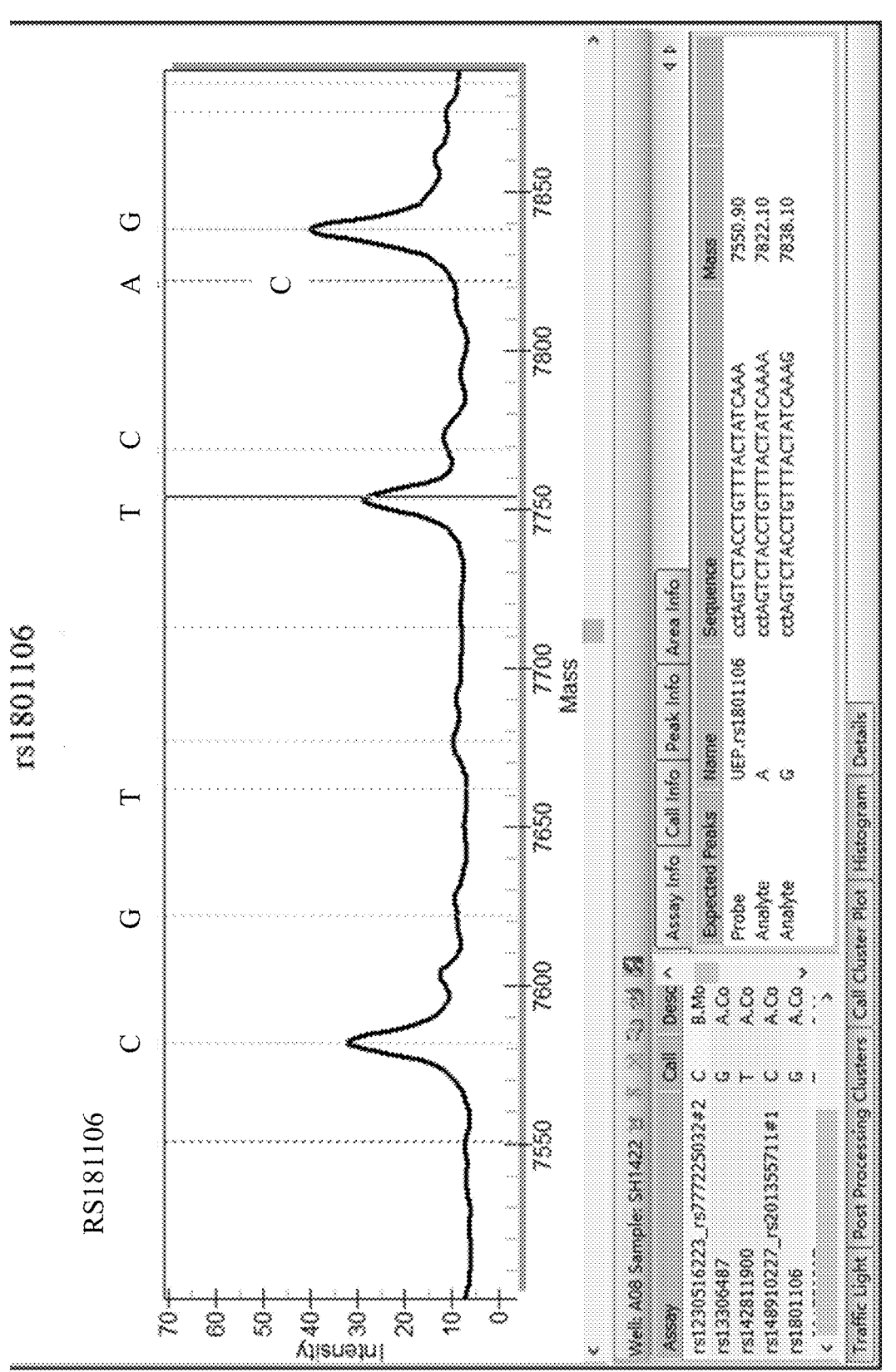
FIG. 10 is a detection mass spectrogram of amplification and detection of the HPA-5 (rs1801106) site by new1 primers provided by Embodiment 4.
Figure 11:
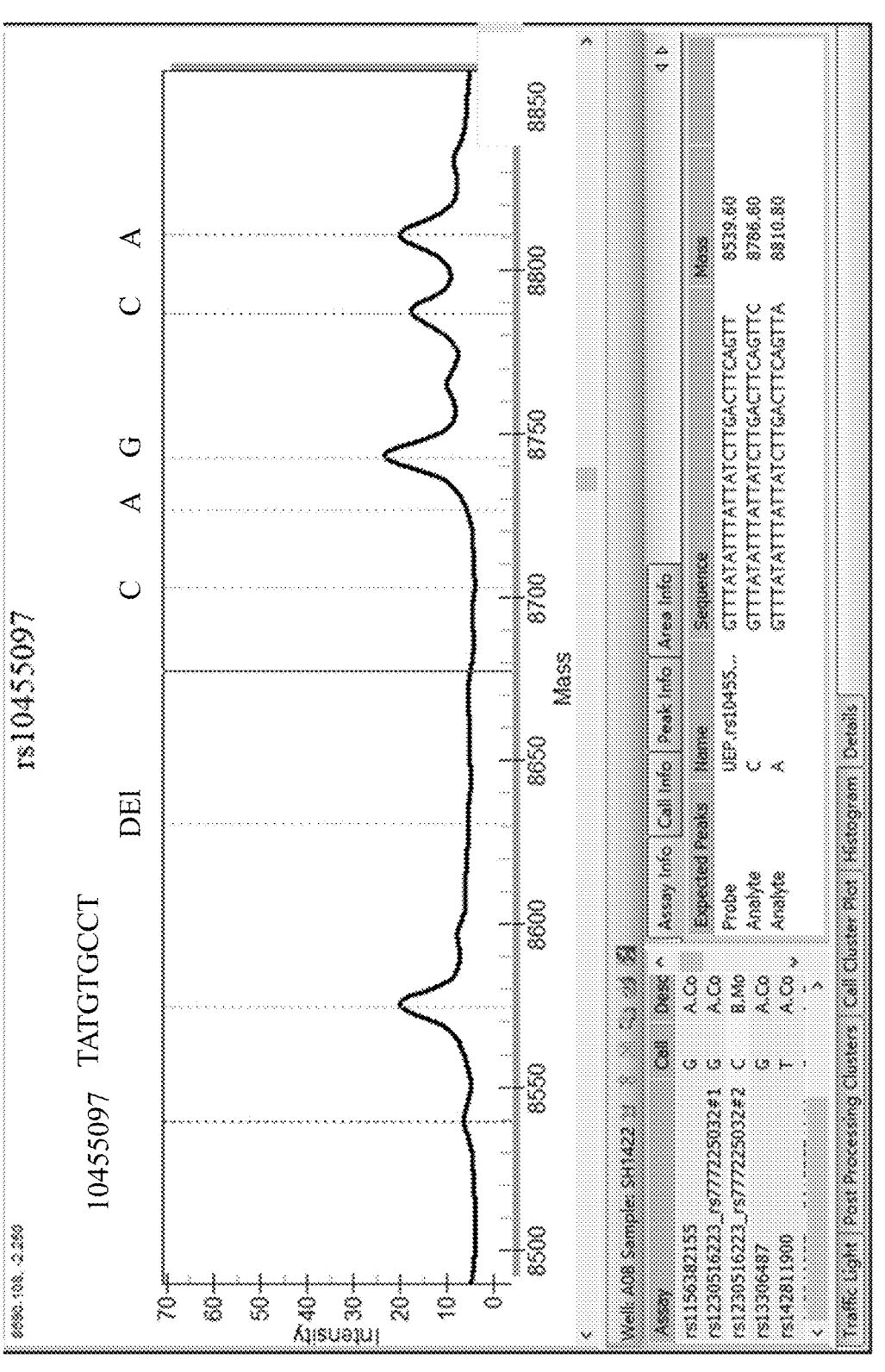
FIG. 11 is a detection mass spectrogram of amplification and detection of the HPA-15 (rs10455097) site by new1 primers provided by Embodiment 4.
Figure 12:
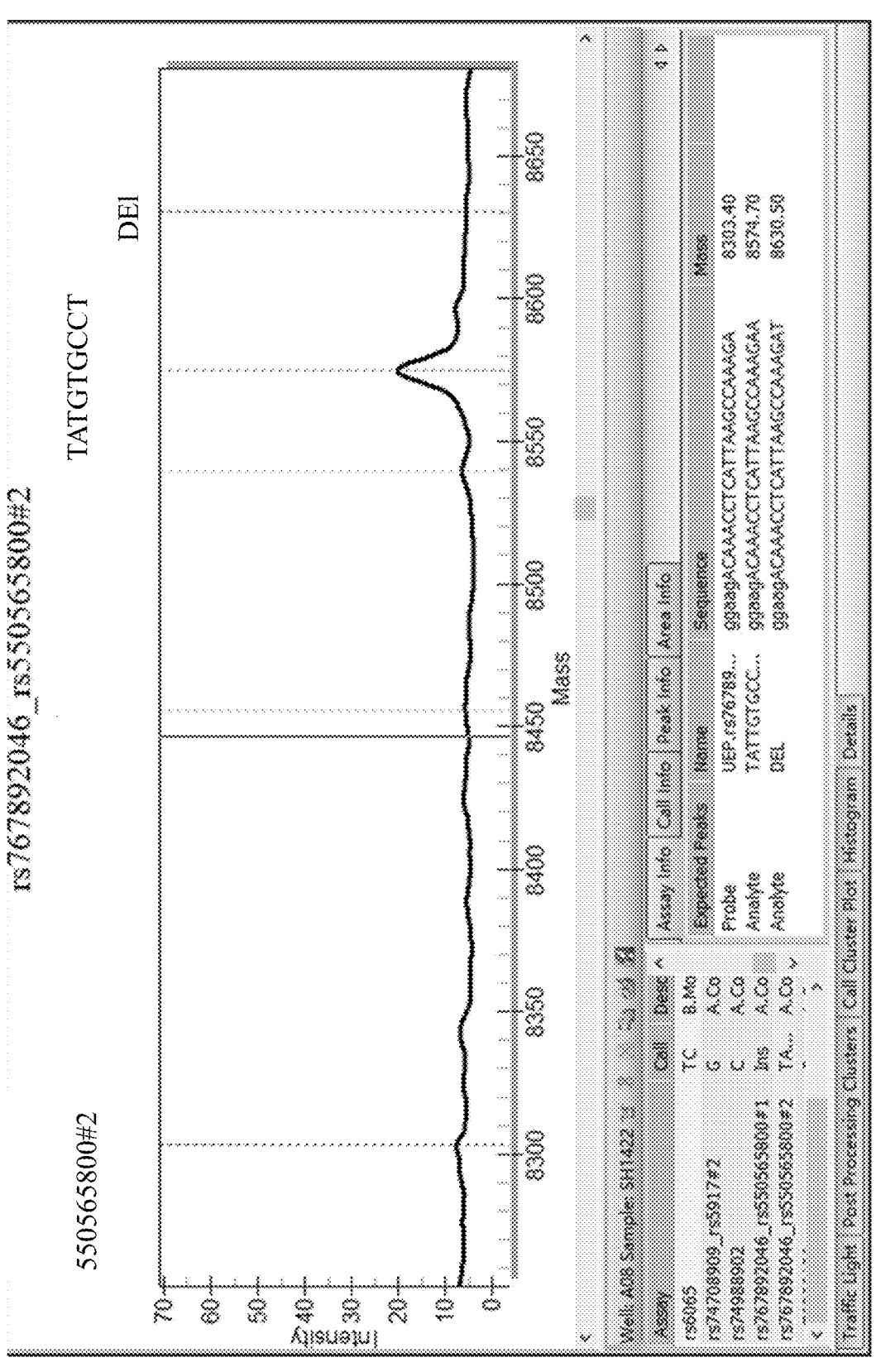
FIG. 12 is a detection mass spectrogram of amplification and detection of the CD36(1) (rs550565800) site by new1 primers provided by Embodiment 4.

| Influence of different primer pairs | | | |
| --- | --- | --- | --- |
| Sites | Serial numbers of primer pairs included in primer combinations | | |
| rs1801106 | old | new1 | new2 |
| rs10455097 | old | new1 | new2 |
| rs550565800 | old | new1 | new2 |
| Amplification results | Three sites cannot be successfully detected (FIGS. 7, 8 and 9) | Three sites can be successfully detected and introduced into a platelet group panel (FIGS. 10, 11 and 12) | rs10455097 is successfully detected, and the remaining two sites cannot be successfully detected |

It can be seen from Tables 21 and 22 that the use of different primer pair combinations has a significant impact on detection results of each site. Only when the primer pair combination of new1 is used, three sites of HPA-5 (rs1801106), (rs10455097), and CD36 (1) (rs550565800) can be successfully detected when 53 sites of the entire panel are detected simultaneously, and simultaneous detection of the overall 53 sites can be successfully carried out.

(2) Change of PCR Conditions (Using a Touchdown Annealing Temperature)

In this embodiment, three annealing temperatures shown in Table 18 are respectively used for PCR, to examine effects of different annealing temperatures on the amplification and detection results of the overall site.

TABLE 23

| Influence of different annealing temperatures | | |
| --- | --- | --- |
| Serial number | Annealing temperature (° C.) | Amplification results |
| 1 | 68-60 | Low conversion efficiency (52% to 85%) |
| 2 | 68-56 | General conversion efficiency (65% to 90%) |

TABLE 23-continued

| Influence of different annealing temperatures | | |
| --- | --- | --- |
| Serial number | Annealing temperature (° C.) | Amplification results |
| 3 | 65-53 | Highest conversion efficiency (75% to 98%) |

It can be seen from Table 23 that when the overall 53 sites are detected, the influence of annealing temperatures is examined again, and it is found that different annealing temperatures still have a great impact on the conversion efficiency of the entire panel during multiple PCR reaction, and the previously determined annealing temperature of 68° C. to 60° C. is still too high, resulting in low conversion efficiency. Therefore, a preferred annealing temperature is 65 to 53° C. in a process of designing a mass spectrometer chip for the entire panel.

(3) Through overall screening and optimization, and by verifying the 53 sites of the entire panel in Embodiment 1 in 400 samples, stable results are obtained, and both detection sensitivity and specificity are very good.

Although the present invention is disclosed above, the present invention is not limited thereto. Any person skilled in the art can make various changes and amendments without departing from the spirit and scope of the present invention. Therefore, the protection scope of the present invention shall be based on the scope defined by the claims.

The invention claimed is:

1. A method for genotyping by mass spectrometry detection comprises the following steps:

(1) using an amplification primers mix to amplify genes from a DNA template by a multiplex PCR reaction;

(2) purifying an amplification product obtained in Step (1) by an alkaline phosphatase;

(3) using an extension primers mix to extend and amplify the purified product in Step (2) by a single base; and (4) conducting sample application on a single-base extended product obtained in Step (3) onto a chip for mass spectrometry detection;

wherein the amplification primers mix and the extension primers are included in a tube, and the amplification primers and the extension primers are as below:

| | SNP sites | Forward primers | Reverse primers | Extension primers |
|---|---|---|---|---|
| CD36 (1) | rs550565800 | SEQ ID NO: 1 | SEQ ID NO: 2 | SEQ ID NO: 3 |
| CD36 (2) | rs75326924 | SEQ ID NO: 4 | SEQ ID NO: 5 | SEQ ID NO: 6 |
| CD36 (3) | rs572295823 | SEQ ID NO: 7 | SEQ ID NO: 8 | SEQ ID NO: 9 |
| CD36 (4) | rs201355711 | SEQ ID NO: 10 | SEQ ID NO: 11 | SEQ ID NO: 12 |
| CD36 (5) | rs148910227 | SEQ ID NO: 13 | SEQ ID NO: 14 | SEQ ID NO: 15 |
| CD36 (6) | rs201765331 | SEQ ID NO: 16 | SEQ ID NO: 17 | SEQ ID NO: 18 |
| CD36 (7) | rs545489204 | SEQ ID NO: 19 | SEQ ID NO: 20 | SEQ ID NO: 21 |
| CD36 (8) | rs142186404 | SEQ ID NO: 22 | SEQ ID NO: 23 | SEQ ID NO: 24 |
| CD36 (9) | rs201759307 | SEQ ID NO: 25 | SEQ ID NO: 26 | SEQ ID NO: 27 |
| CD36 (10) | rs767892046 | SEQ ID NO: 28 | SEQ ID NO: 29 | SEQ ID NO: 30. |

2. The method according to claim 1, wherein the tube further comprises amplification primers and extension primers, and the amplification primers and the extension primers are as below:

| | SNP sites | Forward primers | Reverse primers | Extension primers |
|---|---|---|---|---|
| HPA-1 | rs5918 | SEQ ID NO: 31 | SEQ ID NO: 32 | SEQ ID NO: 33 |
| HPA-2 | rs6065 | SEQ ID NO: 34 | SEQ ID NO: 35 | SEQ ID NO: 36 |
| HPA-3 | rs5911 | SEQ ID NO: 37 | SEQ ID NO: 38 | SEQ ID NO: 39 |
| HPA-4 | rs5917 | SEQ ID NO: 40 | SEQ ID NO: 41 | SEQ ID NO: 42 |
| HPA-5 | rs1801106 | SEQ ID NO: 43 | SEQ ID NO: 44 | SEQ ID NO: 45 |
| HPA-6w | rs13306487 | SEQ ID NO: 46 | SEQ ID NO: 47 | SEQ ID NO: 48 |
| HPA-7w | rs121918448 | SEQ ID NO: 49 | SEQ ID NO: 50 | SEQ ID NO: 51 |
| HPA-8w | rs151219882 | SEQ ID NO: 52 | SEQ ID NO: 53 | SEQ ID NO: 54 |
| HPA-9w | rs74988902 | SEQ ID NO: 55 | SEQ ID NO: 56 | SEQ ID NO: 57 |
| HPA-10w | rs200358667 | SEQ ID NO: 58 | SEQ ID NO: 59 | SEQ ID NO: 60 |
| HPA-11w | rs377302275 | SEQ ID NO: 61 | SEQ ID NO: 62 | SEQ ID NO: 63 |
| HPA-12w | rs375285857 | SEQ ID NO: 64 | SEQ ID NO: 65 | SEQ ID NO: 66 |
| HPA-13w | rs79932422 | SEQ ID NO: 67 | SEQ ID NO: 68 | SEQ ID NO: 69 |
| HPA-14w | HPA-14w | SEQ ID NO: 70 | SEQ ID NO: 71 | SEQ ID NO: 72 |
| HPA-15 | rs10455097 | SEQ ID NO: 73 | SEQ ID NO: 74 | SEQ ID NO: 75 |
| HPA-16w | rs74708909 | SEQ ID NO: 76 | SEQ ID NO: 77 | SEQ ID NO: 78 |
| HPA-17w | rs770992614 | SEQ ID NO: 79 | SEQ ID NO: 80 | SEQ ID NO: 81 |
| HPA-18w | rs267606593 | SEQ ID NO: 82 | SEQ ID NO: 83 | SEQ ID NO: 84 |
| HPA-19w | rs80115510 | SEQ ID NO: 85 | SEQ ID NO: 86 | SEQ ID NO: 87 |
| HPA-20w | rs78299130 | SEQ ID NO: 88 | SEQ ID NO: 89 | SEQ ID NO: 90 |
| HPA-21w | rs70940817 | SEQ ID NO: 91 | SEQ ID NO: 92 | SEQ ID NO: 93 |
| HPA-22w | rs142811900 | SEQ ID NO: 94 | SEQ ID NO: 95 | SEQ ID NO: 96 |

-continued

|  | SNP sites | Forward primers | Reverse primers | Extension primers |
|---|---|---|---|---|
| HPA-23w | rs139166528 | SEQ ID NO: 97 | SEQ ID NO: 98 | SEQ ID NO: 99 |
| HPA-24w | rs281864910 | SEQ ID NO: 100 | SEQ ID NO: 101 | SEQ ID NO: 102 |
| HPA-25w | rs771035051 | SEQ ID NO: 103 | SEQ ID NO: 104 | SEQ ID NO: 105 |
| HPA-26w | rs1156382155 | SEQ ID NO: 106 | SEQ ID NO: 107 | SEQ ID NO: 108 |
| HPA-27w | rs149468422 | SEQ ID NO: 109 | SEQ ID NO: 110 | SEQ ID NO: 111 |
| HPA-28w | rs368953599 | SEQ ID NO: 112 | SEQ ID NO: 113 | SEQ ID NO: 114 |
| HPA-29w | rs544276300 | SEQ ID NO: 115 | SEQ ID NO: 116 | SEQ ID NO: 117 |
| HPA-30w | rs377753373 | SEQ ID NO: 118 | SEQ ID NO: 119 | SEQ ID NO: 120 |
| HPA-31w | rs202229101 | SEQ ID NO: 121 | SEQ ID NO: 122 | SEQ ID NO: 123 |
| HPA-32w | rs879083862 | SEQ ID NO: 124 | SEQ ID NO: 125 | SEQ ID NO: 126 |
| HPA-33w | rs1555572829 | SEQ ID NO: 127 | SEQ ID NO: 128 | SEQ ID NO: 129 |
| HPA-34w | rs777748046 | SEQ ID NO: 130 | SEQ ID NO: 131 | SEQ ID NO: 132 |
| HPA-35w | rs779974422 | SEQ ID NO: 133 | SEQ ID NO: 134 | SEQ ID NO: 135. |

3. The method according to claim 2, wherein the tube further comprises amplification primers and extension primers, and the amplification primers and the extension primers are as below:

| Detected genes | SNP sites | Forward primers | Reverse primers | Extension primers |
|---|---|---|---|---|
| HNA-1 (1) | rs448740 | SEQ ID NO: 136 | SEQ ID NO: 137 | SEQ ID NO: 138 |
| HNA-1 (2) | rs5030738 | SEQ ID NO: 139 | SEQ ID NO: 140 | SEQ ID NO: 141 |
| HNA-2 (1) | rs777225032 | SEQ ID NO: 142 | SEQ ID NO: 143 | SEQ ID NO: 144 |

-continued

| Detected genes | SNP sites | Forward primers | Reverse primers | Extension primers |
|---|---|---|---|---|
| HNA-2 (2) | rs1230516223 | SEQ ID NO: 145 | SEQ ID NO: 146 | SEQ ID NO: 147 |
| HNA-3 (1) | rs147820753 | SEQ ID NO: 148 | SEQ ID NO: 149 | SEQ ID NO: 150 |
| HNA-3 (2) | rs2288904 | SEQ ID NO: 151 | SEQ ID NO: 152 | SEQ ID NO: 153 |
| HNA-4 | rs1143679 | SEQ ID NO: 154 | SEQ ID NO: 155 | SEQ ID NO: 156 |
| HNA-5 | rs2230433 | SEQ ID NO: 157 | SEQ ID NO: 158 | SEQ ID NO: 159. |

4. The method according to claim 1, wherein a final concentration of each primer in the amplification primer mix is 0.1 to 1 μM.

5. The method according to claim 1, wherein the multiplex PCR reaction in Step (1) is as follows:

| Components | Volume (μL) |
|---|---|
| Water, HPLC grade | 0.8 |
| 10 x PCR Buffer with 20 mM MgCl$_2$ | 0.5 |
| 25 mM MgCl$_2$ | 0.4 |
| 25 mMdNTP Mix (dNTP mix) | 0.1 |
| 0.5 to 5 uM Primer Mix | 1 |
| 5 U/μl PCR Enzyme | 0.2 |
| 5 to 20 ng/μL DNA template | 2 |
| Total volume | 5. |

6. The method according to claim 1, wherein the DNA template is a DNA extracted from a blood sample and wherein the DNA template comprises a platelet DNA, a glycoprotein DNA or a neutrophil DNA.

7. The method according to claim 1, wherein an annealing temperature of the multiplex PCR reaction in Step (1) is 65° C. to 53° C.

\*　\*　\*　\*　\*